(12) United States Patent
Manico et al.

(10) Patent No.: US 9,241,872 B2
(45) Date of Patent: Jan. 26, 2016

(54) TIMED SEQUENCE INDICATORS

(71) Applicants: Joseph Anthony Manico, Rochester, NY (US); Kevin Michael Gobeyn, Rochester, NY (US)

(72) Inventors: Joseph Anthony Manico, Rochester, NY (US); Kevin Michael Gobeyn, Rochester, NY (US)

(73) Assignee: EASTMAN KODAK COMPANY, Rochester, NY (US)

(*) Notice: Subject to any disclaimer, the term of this patent is extended or adjusted under 35 U.S.C. 154(b) by 171 days.

(21) Appl. No.: 13/929,829

(22) Filed: Jun. 28, 2013

(65) Prior Publication Data
US 2015/0001123 A1 Jan. 1, 2015

(51) Int. Cl.
*A61J 1/03* (2006.01)
*A61J 7/04* (2006.01)
*G01N 31/22* (2006.01)
*G07C 1/08* (2006.01)

(52) U.S. Cl.
CPC .............. *A61J 1/035* (2013.01); *A61J 7/0409* (2013.01); *G01N 31/225* (2013.01); *G01N 31/229* (2013.01); *G07C 1/08* (2013.01); *G01N 31/22* (2013.01)

(58) Field of Classification Search
CPC ............ B65D 85/00; A61J 1/035; A61J 1/03; A61J 7/0409; G01N 31/225; G01N 31/22; G01N 31/229; G07C 1/08
USPC ............. 206/531, 534, 532, 538, 528; 53/477
See application file for complete search history.

(56) References Cited

U.S. PATENT DOCUMENTS

| | | | | |
|---|---|---|---|---|
| 4,091,921 A * | 5/1978 | Lewis | .......................... | 206/363 |
| 4,945,708 A * | 8/1990 | Curiel | .............................. | 53/411 |
| 5,602,804 A | 2/1997 | Haas | | |
| 6,345,717 B1 * | 2/2002 | Flewitt | .......................... | 206/531 |
| 6,741,523 B1 * | 5/2004 | Bommarito et al. | .......... | 368/327 |
| 6,916,116 B2 * | 7/2005 | Diekmann et al. | ............ | 374/102 |
| 6,968,804 B1 * | 11/2005 | Barbieri et al. | ............... | 116/219 |
| 7,294,379 B2 | 11/2007 | Ko et al. | | |
| 7,808,861 B2 | 10/2010 | Wien | | |
| 2006/0086639 A1 | 4/2006 | Priebe et al. | | |
| 2006/0110835 A1 * | 5/2006 | Gohil | ............................ | 436/169 |

(Continued)

FOREIGN PATENT DOCUMENTS

DE 3028808 3/1982
EP 2 468 283 A1 6/2012

(Continued)

OTHER PUBLICATIONS

"A solvent-based intelligence ink for oxygen", Andrew Mills and David Hazafy, The Royal Society of Chemistry, The Analyst, Jan. 28, 2008, vol. 133, pp. 213-218.

(Continued)

*Primary Examiner* — Steven A. Reynolds
(74) *Attorney, Agent, or Firm* — David A. Novais; Nelson A. Blish; Kevin E. Spaulding

(57) ABSTRACT

A containment system for packaging a plurality of products that are to be accessed in a predetermined sequence. The containment system includes a plurality of product compartments that each holds at least one of the plurality of products. Indicators having a gas reactive material that changes appearance after a predetermined period of time of exposure to ambient air are deployed when gas cover seals are removed or broken to access a product in the product compartment.

15 Claims, 15 Drawing Sheets

(56) References Cited

U.S. PATENT DOCUMENTS

| | | | |
|---|---|---|---|
| 2009/0107873 A1* | 4/2009 | Cotton et al. | 206/531 |
| 2010/0143675 A1 | 6/2010 | Guckian et al. | |
| 2010/0193468 A1 | 8/2010 | Burrows et al. | |
| 2010/0221468 A1 | 9/2010 | Khan et al. | |
| 2011/0139655 A1 | 6/2011 | Cochran et al. | |
| 2014/0326635 A1* | 11/2014 | Uetake, Kazuaki | 206/531 |

FOREIGN PATENT DOCUMENTS

| | | |
|---|---|---|
| JP | 10319148 | 12/1998 |
| JP | 2009-143591 | 7/2007 |
| WO | WO 97/20754 | 6/1997 |
| WO | WO 2004/005424 | 1/2004 |
| WO | WO 2010/068527 | 6/2010 |

OTHER PUBLICATIONS

"Oxygen indicators and intelligent inks for packaging food", Andrew Mills, The Royal Society of Chemistry, Chemical Society Review, 2005, vol. 34, pp. 1003-1011.

"An intelligence ink for oxygen", Soo-Kean Lee, Andrew Mills and Anne Lepre, The Royal Society of Chemistry, Chemical Communications, 2004, Issue 17, pp. 1912-1913.

"UV-Activated Luminescence/Colourimetric $O_2$ Indicator", Andrew Mills, Cheryl Tommons, Raymond T. Bailey, M. Catriona Tedford and Peter J. Crilly, International Journal of Photoenergy, vol. 2008, Article ID 547301.

* cited by examiner

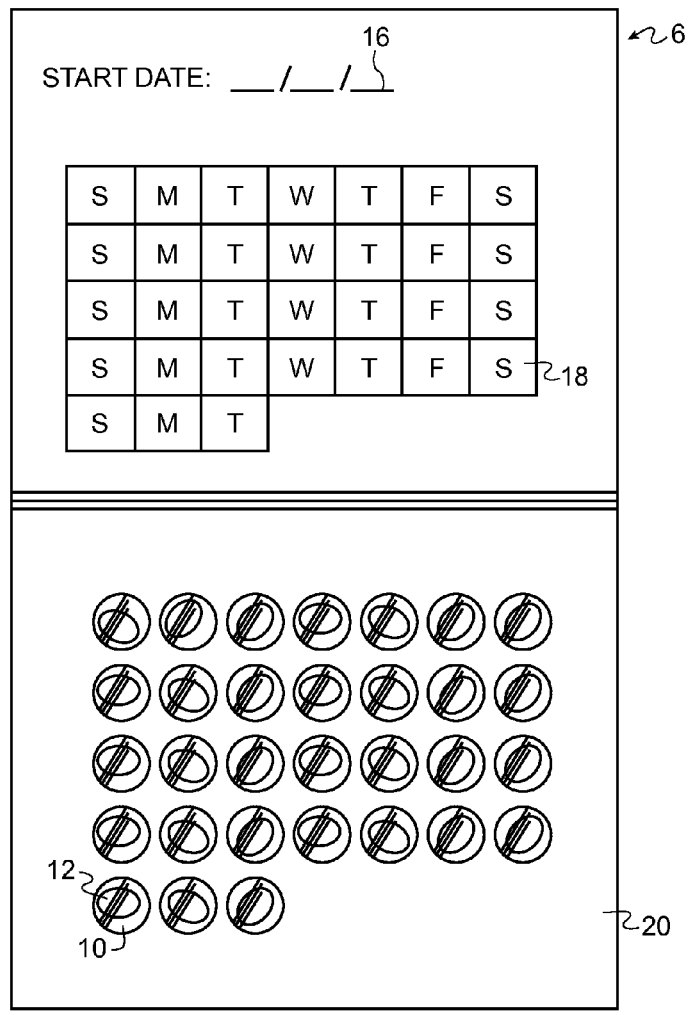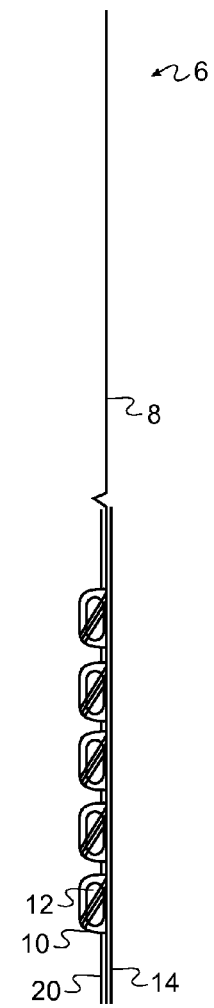
FIG. 1a
(PRIOR ART)
FIG. 1b
(PRIOR ART)

TIMED SEQUENCE INDICATORS

FIELD OF THE INVENTION

The present invention relates to the field of product packaging and/or service offerings, and more particularly, to product packaging and/or service offerings that incorporate user instructions and/or notifications.

BACKGROUND OF THE INVENTION

The packing of individual products in individual containers sized for single use is becoming increasingly common for a variety of products that have previously been packaged in bulk forms. Because this transition is occurring most rapidly with respect to medical products, this type of packaging is often referred to as unit dose packaging. In some types of unit dose packaging each product has a separate container. However, this can lead to inefficiencies in manufacturing and can complicate handling by requiring the management of a multiplicity of individual items.

Accordingly, another type of unit dose packaging has emerged having a plurality of separate non-reusable unit dose containers that are physically linked often in a manner that allows the separation of the unit dose containers if later desired. For example, it is commonly known to package a plurality of pills using what is known as a blister pack. This approach provides a form of unit dose packaging that can be manufactured and handled more efficiently than separate but individual packages of pills.

Various examples of blister packs are described in WO 97/20754, entitled: "Reinforced Blister Pack". As is noted therein, blister packs generally comprise a pattern of blisters formed in a sheet of substantially impermeable deformable plastics material, each blister defining a cavity for the containment of a tablet. The open face of the blister is closed with a film cover, usually a thin, tearable metal foil or a peel-off film. The film cover can either be easily ruptured, or the film can be easily peeled away from the blister. In use either the blister is compressibly deformed so as to force the tablet therein out though a rupturable film, or the film is peeled off and the tablet is removed from the cavity. Generally the deformable material is a stiff but relatively flexible material such as a plastic material or a plastic material laminate or plastic material metal foil laminate. WO 97/20754 provides a blister pack having reinforced material between blisters to confer rigidity relative to flexing deformation of the blister pack and is said to facilitate handling by users with weak or deformed hands.

FIG. 1a is a front view and FIG. 1b is a side view of a prior art blister pack 6 used for unit dose packaging of pills 12. In the example of FIGS. 1a and 1b, blister pack 6 provides a container tray 8 with a plurality of individual containment areas 10 that can each receive one of thirty one pills 12 and a film 14 that is joined to container tray 8 and support 20 to contain pills 12 within containment areas 10. This arrangement conveniently allows packaging of an entire one month course of individual doses of pills 12. The embodiment of prior art blister pack 6 illustrated in FIGS. 1a and 1b is known in the art as a "push through pack" because it is necessary to push pills 12 through film 14 in order to access pills 12. The process of pushing pills 12 through film 14 alters prior art blister pack 10 in a variety of ways (for example, leaving an opening in film 14 at the containment area 10 from which pill 12 has been pushed). Such alterations provide a clear indication of which of pills 12 have been used, and which pills 12 remain available for use.

However, when pills 12 must be taken in a sequence and at particular times relative to each other, it is necessary to carefully prepare printed instructions and warnings. It is also necessary that the user carefully review and interpret the instructions, and properly execute the instructions to ensure that pills 12 are taken according to a desired treatment regime. This places a heavy burden on the manufacturer of pills 12 and upon the user of user pills 12 to make sure that the pills are used and taken in accordance with these instructions. Even when manufacturers and users both act diligently there can be confusion and errors in the timing, sequence and quantity of pills 12 to be taken which can negatively impact the efficacy of treatment. For example while prior art blister pack 6 requires a user to push pills 12 through film 14, leaving a clear indication that certain of pills 12 have been accessed, there is no inherent indication of when pills 12 were accessed.

Accordingly, in the example of prior art blister pack 6 shown in FIGS. 1a and 1b, the manufacturer provides a variety of printed tools to help a user to resolve such problems. As shown, prior art blister pack 6 has a printed area 16 in which starting dates can be written and a calendar 18 which can be used to provide a user with some guidance on this point. However, even where such tools are used, a user of pills 12 can be confused as to which day they are in with respect to a multi day course of treatment. That is, a user who is to take a daily course of one pill per day can observe that prior art blister pack 6 has two containment areas 10 without pills 12 but cannot recall whether today is the second or third day of a course of treatment and will be left with weighing the risks of taking too much medication or too little medication today. Further, such expedients rely both on the correct entry and use of such information. Over the course of a thirty one day treatment regime confusion is still possible particularly where such users are in pain, fatigued, or taking medications that impair or otherwise limit their analytical abilities.

In other examples, some pills 12 must be taken according to a more rigorous schedule. For example, in some cases pills 12 are to be taken within 24 hours of each other during the course of therapy. However, problems can arise if a first one of pills 12 is taken at 6:00 a.m. on a first day of treatment and a second one of pills 12 is taken at 6:00 p.m. on a second day of treatment. Conversely, where a user is subject to a treatment regime that requires that a user take pills 12 no sooner than 24 hours apart, the tools and arrangement of the prior art blister pack 6 leave open the possibility that this regime will not be followed. For example, a user can dutifully use the tools on prior art blister pack 6 while taking a first one of pills 12 at 6 p.m. on a first day of treatment, and a second one of pills 12 at 6 a.m. on a second day treatment such that pills 12 are not taken according to the regime prescribed.

The individual packaging of pills 12 in prior art blister pack 6 can also be construed by some users as impliedly suggesting that pills 12 are to be taken one at a time. However, in some cases a course of pills 12 may require that a user take pills 12 in different doses over the course of treatment such that, for example, on a first day two pills 12 must be taken while on each of the following three days only one pill 12 is to be taken. Additionally, in some cases pills 12 can be taken according to more than one possible sequence or schedule. For example, when certain pills 12 are to be used on a periodic schedule, optional instructions can be provided to allow a user to consume a first one of pills 12 and then, if symptoms for which the pills 12 are being taken persist, the user can take a second pill 12 within a shorter than normal period. In such cases great care must be taken in preparing the printed instructions for such packaging and the risk of error arising through misreading instructions, misinterpreting instructions or inaccurate recollection of consumption cannot be eliminated.

This places a burden on a user to carefully manage usage of the products to accurately read, understand and follow instructions on prior art blister pack 6, and, as necessary, to set reminder systems, checklists or other processes to provide context in which to interpret the indications provided by prior art blister pack 6. Here too, while many users are capable of doing this, many pills 12 are intended for use by people whose ability to do so is limited by pain, fatigue, impaired judgment or the like. Additionally, there is the risk that a user may misunderstand the instructions, forget the instructions or specific details of the instructions.

Automatic reminder systems such as mechanical and electronic timers and clocks can be used to help remind a user as to when the user is to access the next unit dose. These devices require that the user secure such a timer and repeatedly reset the timer or otherwise program the timer so that the timer provides reminders at appropriate times. Mechanical timers have to be periodically rewound and electronic timers require batteries and need to be programmed by the user employing user interfaces with limited buttons and displays. Further, there is no inherent physical or logical integration between such timers and pills 12.

Also, automatic timers are not easily integrated into blister packs 6 as the physical format, low cost, and automated production of prior art blister packs 6 is made possible through the use of conventional blister pack manufacturing lines know in the art as "blisterlines". These blisterlines use a process that involves laminating multiple films to form a container tray 8 having appropriately sized containment areas 10, loading pills 12 and applying film 14 to container tray 8. The blisterline tooling has been highly optimized to achieve greater productivity and to minimize the cost of manufacturing conventional blister packs 6. Accordingly such tooling cannot easily be adapted in the many ways that would be required to allow conventional blisterlines to incorporate automatic mechanical or electronic timers as these timers add significant cost, size, and complexity to such tooling.

Alternatively, it is possible for a user to use reusable pill management devices such as the MedReady 1600, sold by MedReady Inc., Torrance, Calif., USA, in which a user stores pills in separate containers that are linked to a timer that indicates when the contents of container are to be used. However, this approach requires the user to transfer pills 12 from the prior art blister pack 6 to the purchased device and then properly load and configure the device to the time period required. This creates risks that pills 12 can be lost, mixed, or degraded due to exposure to atmospheric gasses and humidity.

It will be appreciated that the problems associated with prior art blister packs 6 used for medical purposes exist more generally across a wide variety of products having a combination of individually packaged components that must be used in a particular sequence and at particular times in order to achieve desired results. Indeed, a wide variety of common consumer products include blister packed items or items that can potentially be packaged in a blister pack and that require careful adherence to potentially confusing instructions which require careful adherence to a sequence of activities; where certain activities are to be performed at predetermined timings relative to each other in order to achieve desired results. Examples of this include, but are not limited to, self assembled furniture kits, ingredient packages, repair kits, emergency kits, chemical preparation kits and the like.

What is needed in the art are new product containment systems that contain products to be used collectively to accomplish a result and that are to be used in a particular sequence and with particular timings.

SUMMARY OF THE INVENTION

The present invention accordingly relates to a containment system for a plurality of products that are to be accessed in a predetermined timed sequence. The containment system comprises a substrate with a plurality of product compartments which each have a volume sufficient to receive at least one of a plurality of products. The substrate further includes a plurality of atmospheric gas conduits each leading from one of the product compartments to a gas sensitive indicator window chamber. The containment system further comprises a plurality of gas sensitive indicators having a gas reactive material that changes appearance at a predetermined time after exposure to ambient air when gas cover seals are removed or broken to access a product in the product compartment.

The present invention further relates to a containment system for a plurality of products that are to be accessed in a timed sequence that comprises: a plurality of product compartments, with each of the product compartments being adapted to hold at least one of the plurality of products; a plurality of gas sensitive indicators adapted to change appearance after exposure to ambient air, at least one of the gas sensitive indicators being located within a gas sensitive indicator window volume; and a plurality of atmospheric gas conduits each leading from one of the product compartments to one of the gas sensitive indicator window chambers, such that an exposure of one of the product compartments to gain access to a product in the one product compartment allows atmospheric gas to flow through at least one of the plurality of atmospheric gas conduits that leads from the exposed product compartment to expose at least one of the gas sensitive indicators. The at least one gas sensitive indicator exposed to ambient air being arranged to change appearance in a manner that indicates that at least one next product in the timed sequence is to be accessed.

The present invention further relates to a method of manufacturing a containment system having time-based visual indicators which comprises: providing at least two gas sensitive indicators on a substrate, with each of the at least two indicators providing an indication directed to an adjacent space on the substrate and being adapted to change appearance at a predetermined time after exposure to ambient air; attaching user removable, gas barrier film segments substantially aligned with and covering the indicators and the substrate; and sealing the film segments to the substrate so that the indicators are isolated from ambient air.

BRIEF DESCRIPTION OF THE DRAWINGS

FIG. 1a is a front view of a prior art blister pack;
FIG. 1b is a side view of the prior art blister pack of FIG. 1a.

DETAILED DESCRIPTION OF THE INVENTION

Figure 8:
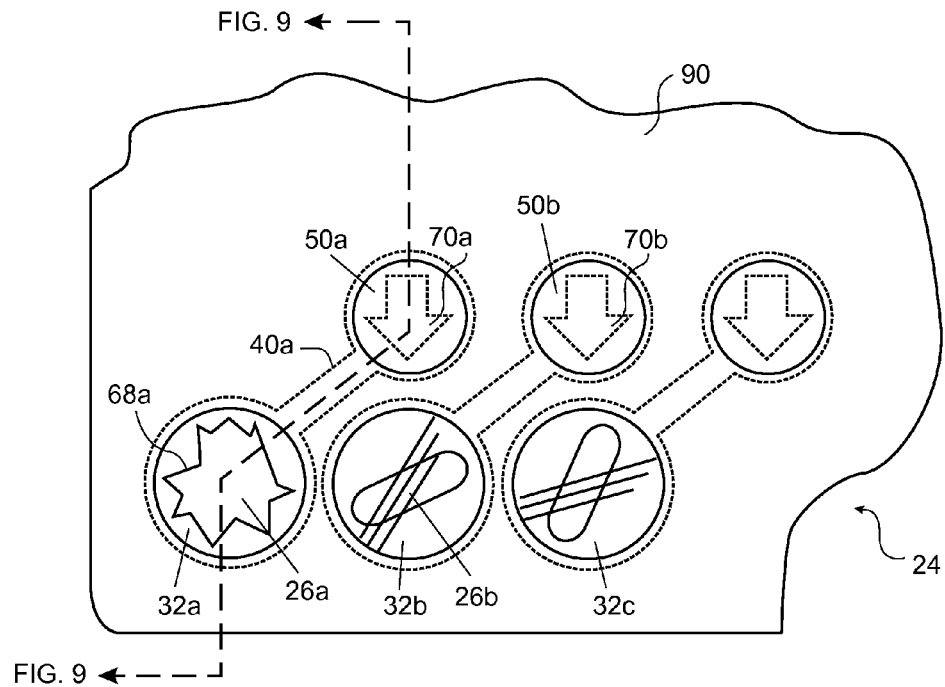
FIG. 8 is a cutaway view of the product containment system of FIG. 6.
Figure 9:
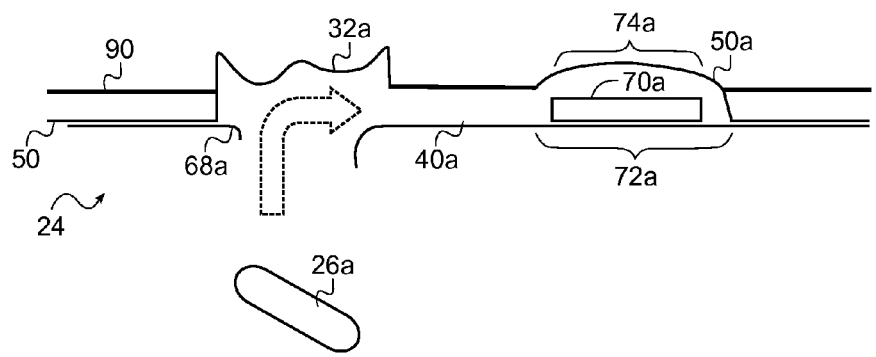
FIG. 9 is a section view of the product containment system of FIG. 6 taken as shown in FIG. 8.
Figure 10:
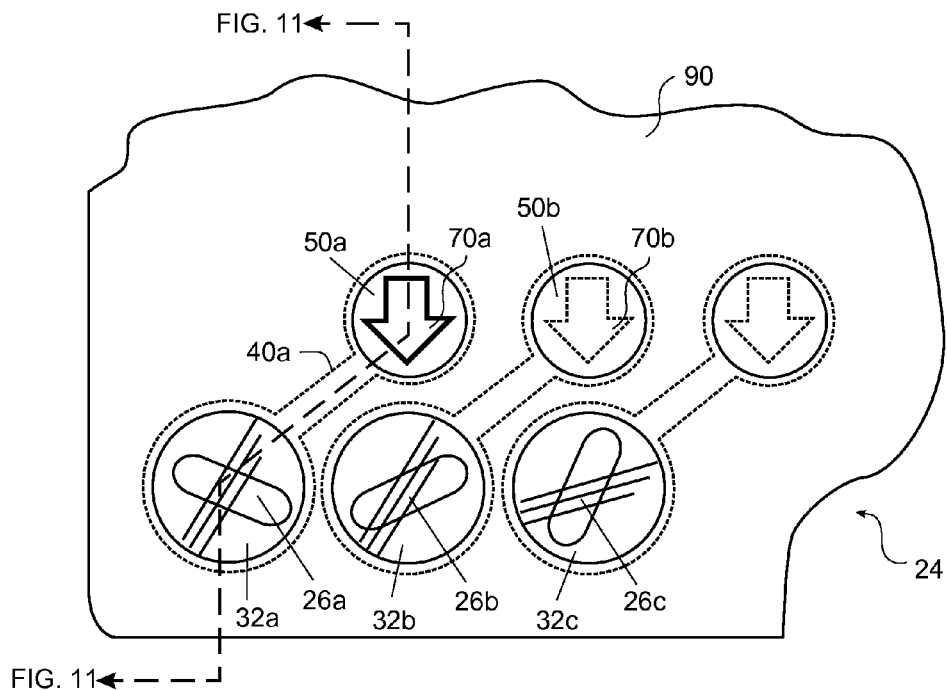
FIG. 10 is a top cutaway view of the product containment system of FIGS. 2-9 at a predetermined time after a product has been accessed.
Figure 11:
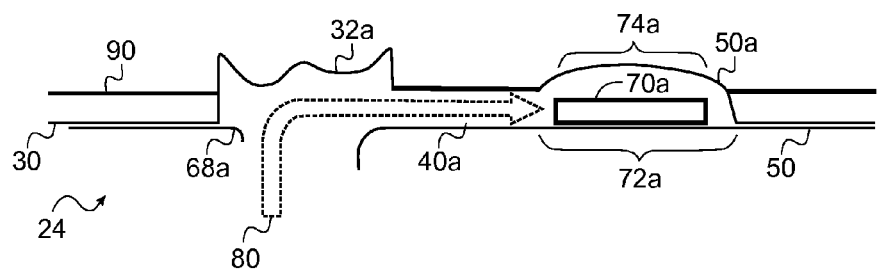
FIG. 11 is a section view of the product containment system at the predetermined time after a product has been accessed taken as shown in FIG. 10.

Referring now to the drawings, wherein like reference numerals represent identical or corresponding parts throughout the several views, FIGS. 2-11 illustrate a first embodiment of a product containment system 24 in accordance with the present invention. In FIGS. 2-5 product containment system 24 is illustrated in an unused state; in FIGS. 6-9 product containment system 24 is illustrated immediately after a first product 26a in a sequence of products has been accessed; and FIGS. 10 and 11 illustrate product containment system 24 at a time when a next product 26b in a sequence of products is to be accessed.

Figure 2:
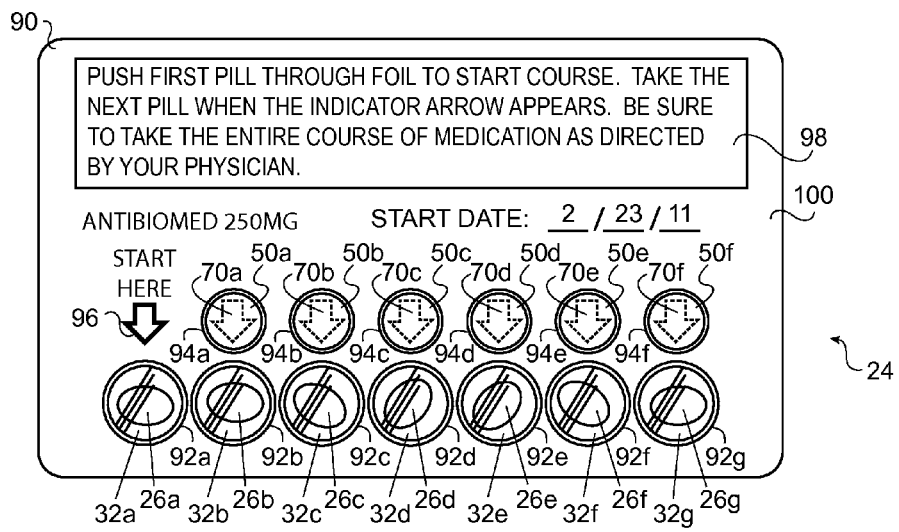
FIG. 2 is a front view of a one embodiment of a product containment system according to the present invention.
Figure 3:
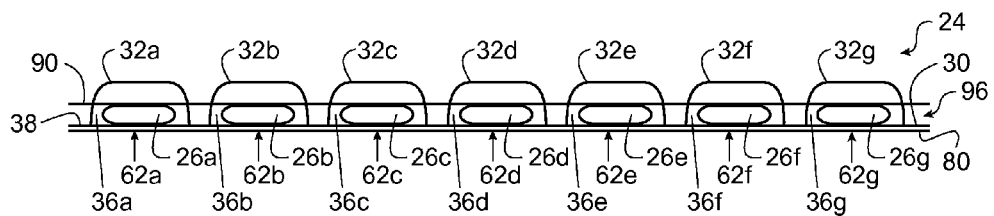
FIG. 3 is a bottom elevation view of the product containment system of FIG. 2.
Figure 4:
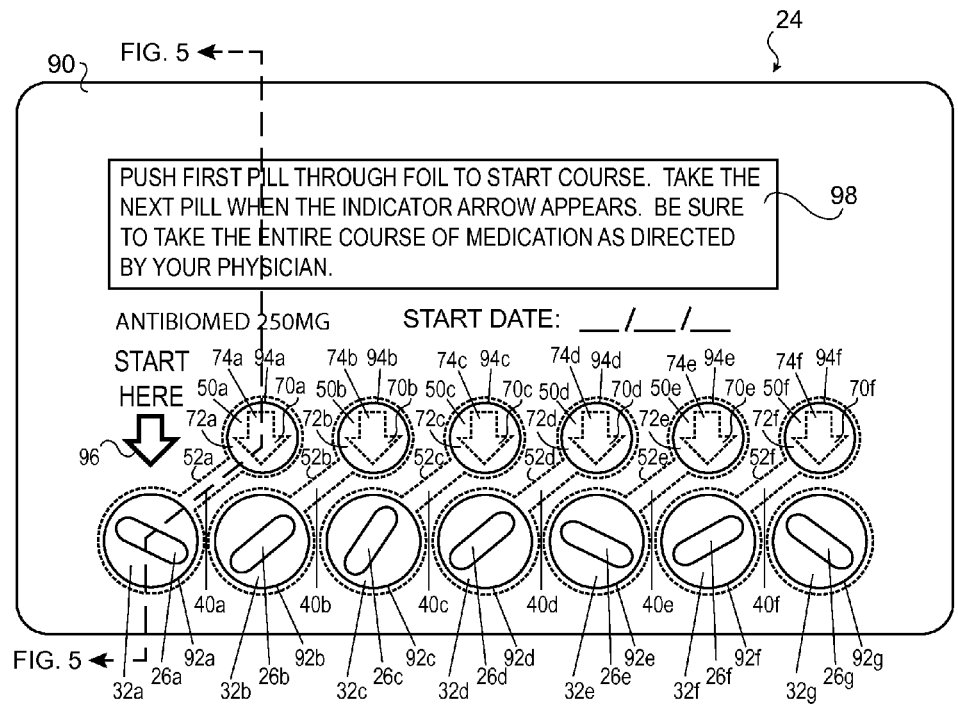
FIG. 4 is a further front view of the product containment system of FIG. 2.

FIGS. 2-5 respectively show a top view of product containment system 24, a bottom elevation view of product containment system 24, a further top view of product containment system 24, and a section view of product containment system 24 taken as indicated in FIG. 4. In this embodiment, product containment system 24 is used to hold a plurality of products 26a-26g. Products 26a-26g can be, for example, pills. However, the present invention is not limited to pills and products 26a-26g can be any type of product that needs to be dispensed in sequence such as a timed sequence. In this example, products 26b-26g are to be used in a predetermined sequence after a product 26a is used, and each product in the sequence is used at a predetermined time after a preceding one of products 26a-26g is used.

In this embodiment, product containment system 24 has a substrate 30 with a plurality of product compartments 32a-32g. Product compartments 32a-32g each have a volume sufficient to receive at least one of the plurality of products 26a-26g, and a compartment opening 36a-36g at a front side 38 of substrate 30 through which products 26a-26g can be moved into and out of product compartments 32a-32g. Substrate 30 also provides a plurality of gas conduits for each product compartment 32a-32g. FIG. 4 shows gas conduits 40a-40f respectively for compartments 32a-32f. Each conduit 40a-40f links each of product compartments 32a-32f to one of a plurality of window chambers 50a-50f. Window chambers 50a-50f are transparent or translucent portions of substrate 30 through which the appearance of one of a plurality of indicators 70a-70f such as gas sensitive indicators can be observed. A film 60 is bound to back side 38 of substrate 30. Film 60 encloses product compartments 32a-32g, conduits 40a-40f and window chambers 50a-50f creating window chamber volumes 52a-52f between film 60 and substrate 30 that are connected to product compartments 32a-32g by way of conduits 40a-40f, respectively.

An optional cover sheet 90 (FIGS. 2-3) is also shown having, in this embodiment, holes 92a-92g that are patterned and sized to allow cover sheet 90 to slide over product compartments 32a-32g until cover sheet 90 is pressed against at least a part of front side 38 of substrate 30, such that product compartments 32a-32g protrude from holes 92a-92g. A back side 96 of cover sheet 90 is typically adhesively bound to front side 38 of substrate 30.

In the embodiment illustrated in FIGS. 2-5, substrate 30 comprises a polymeric material that is impermeable or substantially impermeable to ambient air 80 (FIG. 5) surrounding product containment system 24. Film 60 is made from a thin film of a metallic foil such as an aluminum foil or other metallic foil and is likewise impermeable or substantially impermeable to ambient air 80. Accordingly, when film 60 is bound to front side 38 of substrate 30, film 60 creates a plurality of gas seals 62a-62g (FIG. 3) each sealing one of product compartments 32a-32g against the flow of ambient air 80. Film 60 also seals window chambers 50a-50g and gas conduits 40a-40f against ambient air 80 while creating enclosed environments such as enclosed environment 82a shown in FIG. 5 where gas can flow between connected ones of product compartments 32a-32g, gas conduits 40a-40f and window chambers 50a-50f. Essentially, the product compartments 32a-32g can form sealed cavities that can be arranged in, for example, at least linear array, a matrix pattern or another type of pattern based on the shape of the product containment system.

In other embodiments, thin film 60 can take other forms and comprise, for example and without limitation, a polymeric film or a fibrous material such as paper that is impermeable or substantially impermeable to ambient air 80. Film 60 can have one or more surfaces with one or more layers of additional material thereon. Examples of such additional material include but is not limited to adhesives, primers, sealants, toners, dyes, protective materials, oxygen scavengers and the like. These layers can be applied by way of coating, thermal transfer, or printing for example.

In the embodiment of FIGS. 2-5, indicators 70a-70f are formed on film 60 in indicator portions 74a-74f. Indicator portions 74a-74f, in turn are positioned within visible areas 72a-72f of film 60 that can be observed through window chambers 50a-50f. In other embodiments indicators 70a-70f can be formed in whole or in part on window chambers 50a-50f.

Indicators 70a-70f have or are made of a gas reactive or sensitive material that changes from a first appearance to a second appearance after a predetermined time after exposure to gasses in ambient air 80. In the embodiment shown in FIGS. 2-5, the presence of the gas reactive or sensitive material in indicators 70a-70f causes indicators 70a-70f to have a first appearance causing indicator portions 74a-74f to be difficult to visually discriminate from other portions of visible areas 72a-72f. In this regard, in this embodiment, indicators 70a-70f can have a first appearance that causes indicator portions 74a-74f to be identical, consistent with, to match, or correspond to or to complement other portions of visible areas 72a-72f, so as to limit the extent to which indicator portions 74a-74f have an appearance that is different from that of other portions of visible areas 72a-72f.

As will be discussed in greater detail below, when indicators 70a-70f have a second appearance, indicators 70a-70f cause indicating portions 74a-74f to have an appearance that does not match the appearance of remaining portions of visible area 72a-72f, such as by creating contrast differences between indicating portion 74a and other portions of visible area 72a, by creating inconsistent colors, or by changing in any other way to cause the appearance of the indicating portions 74a-74f to be visually distinct from the appearance of the viewable area.

In other embodiments, indicators 70a-70f can have a first appearance with indicating portions 74a-74f appearing visually inconsistent with the appearance of other portions of visible areas 72a-72f, and a second appearance that is consistent with that of other portions of visible areas 72a-72f. Other arrangements are also possible.

Exposure of the gas sensitive material in indicators 70a-70f can cause indicators 70a-70f to change appearance in any of a number of ways including but not limited to causing a change in the reflectance, absorbency or transmissivity of indicators 70a-70f. For example, the change in gas sensitive material caused by exposure to ambient air 80 can create color changes, reflection pattern changes, or optical density changes or any other changes that can cause or create a visually distinct difference in the appearance of what is visible to an observer through window chambers 50a-50f. Additionally, and without limitation, indicators 70a-70f can have a gas sensitive material that serves as a medium that combines with more than one gas or that cause a combination between more than one gas in ambient air 80 to form combinations that change colors, reflectivities, or transmission characteristics of indicators 70a-70f. In other embodiments, the gas reactive material can comprise a substrate on which biological agents can grow when supplied with oxygen and/or humidity when exposed to atmospheric air so that the appearance change occurs as a product of the growth of a colony of such biological agents. A wide variety of gas sensitive materials can be used for the purposes described herein and several of these materials are described in greater detail below.

As used in this embodiment, ambient air 80 can be understood to mean atmospheric air including at least nitrogen, oxygen, carbon dioxide and water vapor, and in this embodiment the gas reactive material that is selected to cause indicators 70a-70f to change from the first appearance to the second appearance after a predetermined exposure to one or more of these gasses.

Figure 5:
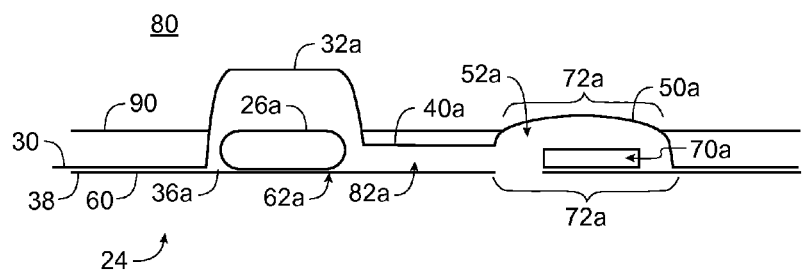
FIG. 5 is a section view of the product containment system of FIG. 2 taken as shown in FIG. 4.

As is shown in FIG. 5, when substrate 30 and film 60 are joined together a portion of film 60 provides a gas seal 62a between a portion of film 60 and portions of substrate 30 forming product compartment 32a, conduit 40a, and window chamber 50a. This in turn creates an enclosed environment 82a within which indicator 70a is protected from exposure to gasses in ambient air 80 that can cause indicator 70a to change appearance. Similarly, other gas seals 62b-62g are formed between portions of film 60 and portions of substrate 30 forming product compartments 32b-32f, conduits 40b-40f, and window chambers 50b-50f. Additionally, a seal 62g is provided between a portion of film 60 and a portion of substrate 30 forming product compartment 32g.

Product containment system 24 is of a push through type. Accordingly, cover sheet 90 can provide starting instructions 98 and optionally a section 100 to enter a start date for administering the product as well as the name of the product, which can be printed using conventional printing technologies on cover sheet 90. Cover sheet 90 can also include instructions to the user such as "Start Here" with an arrow 96 pointing toward product compartment 32a which contains a first product 26a in the sequence of products 26a-26f. This can also be printed on the cover sheet 90 using conventional printing technologies. Arrow 96 also provides the advantage of being an example for the user to observe in order to recognize the subsequent indicators that will appear after the predetermined time period has elapsed. The user, following the instructions can remove product 26a from product compartment 32a by pressing product 26a against thin film 60 to create a disruption 68a (FIG. 6) in gas seal 62a through which product 26a can be removed from product containment system 24.

In this regard, product compartments 32a-32g are collapsible and film 60 and seals 62a-62g are arranged so that a pressure that is sufficient to collapse one of product compartment 32a-32g is also sufficient to drive products 26a-26g through seals 62a-62g respectively. This can be done, for example, by rupturing film 60 at gas seals 62a-62g or by breaking a bond between film 60 and substrate 30 at gas seals 62a-62g. Substrate 30, film 60 and seals 62a-62g otherwise provide sufficient structural strength to hold products 26a-26g within product compartments 32a-32g when exposed to a range of forces that product containment system 24 may be exposed to during incidental contact that arises during manufacture, packaging, retail sale and pre-use transportation to a retailer and to a user.

Figure 6:
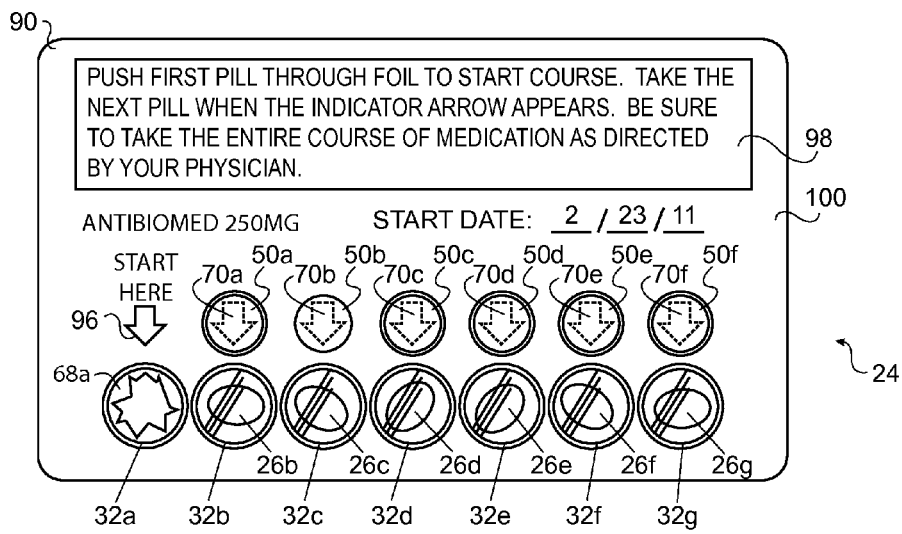
FIG. 6 is a front view of the embodiment of a product containment system shown in FIGS. 2-6 immediately after a product has been accessed.
Figure 7:
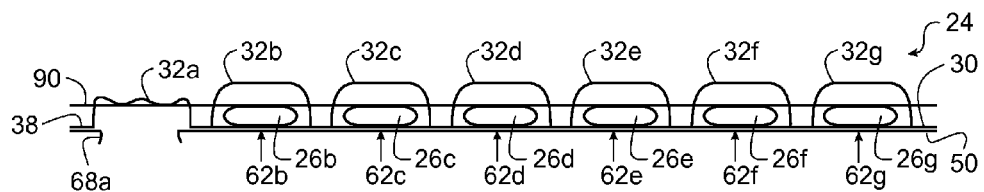
FIG. 7 is a bottom elevation view of the product containment system of FIG. 6.

FIG. 6 shows a top view of the embodiment of product containment system 24 of FIGS. 2-5 immediately after a product 26a has been accessed. FIG. 7 illustrates a bottom elevation view of product containment system 24 immediately after a product 26a has been accessed. FIG. 8 illustrates a cutaway view of the product containment system 24 immediately after a product 26a has been accessed. FIG. 9 illustrates a cross section of the cutaway view of the product containment system 24 immediately after a product 26a has been accessed. FIGS. 10 and 11 illustrate product containment system 24 at a predetermined time after product 26a has been accessed.

As is illustrated in FIGS. 6-9, when a product 26a is accessed, disruption 68a is formed in seal 62a that allows ambient air 80 to be exchanged with any gasses in product compartment 32a. This also allows gasses in ambient air 80 to flow through conduit 40a to window chamber 50a by way of conduit 40a. This begins an exposure of the gas reactive material in indicator 70a that will cause indicator 70a to change from a first appearance to a second appearance at a predetermined time after disruption 68a is formed in seal 62a.

In this embodiment indicator 70a is arranged to indicate at least one of the plurality of products 26b-26f in the predetermined sequence that is to be accessed next. Here, this is done by positioning indicator 70a and window chamber 50a proximate to product compartment 32b in which a next product 26b in the sequence of products 26b-26g is contained (FIGS. 6 and 8). It will be appreciated that use of conduits such as conduit 40a, makes it possible to physically separate the physical location of window chamber 50a from the physical location of product compartment 32a, and to position window chamber 50a in a location that is proximate to product compartment 32b. In this way compartment 32b and the remaining compartments 32c-32g remain sealed from ambient air 80. This proximity helps to avoid confusion as to which product is to be accessed next and is made possible through the use of conduits 40a-40f.

Indicators 70a-70f can also optionally be arranged to supplement the proximity based indication of product compartments 32b-32g by being patterned to further help to clarify which of product compartments 32b-32g are to be used next. In the embodiment of FIGS. 2-9 this is done by shaping indicators 70a-70f in the form of an arrow that is directed toward product compartments 32b-32g. Similarly, in this embodiment, indicator 70b is likewise shaped in the form of an arrow that points toward product compartment 32b and by shaping the remaining indicators in similar fashion. This can help to visually link individual ones of indicators 70a-70f and individual ones of product compartments 32b-32g respectively.

In other embodiments, indicators 70a-70f can also optionally be shaped in other ways to visually link the product compartments. For example, individual ones of indicators 70a-70f can be patterned to have text or graphic symbols that visually correspond with text and graphic symbols associated with individual ones of product compartments 32a-32g. In still other embodiments, indicators 70a-70f can be mapped to correspond to the shapes of distinctly shaped products 26a-26g or to correspond to distinctly shaped product compartments 32b-32g such as by providing indicators 70a-70f that are patterned in distinct shapes that correspond to distinctly shaped ones of product compartments 32b-32g. Similarly, in other embodiments, a plurality of different colors can be optionally used at each of indicators 70a-70f that correspond to a plurality of different colors used at each of product compartments 32b-32g It will be appreciated from the description above that the act of accessing one of products 26a-26g that is stored in product containment system 24 automatically initiates processes that will cause one of indicators 70a-70f to indicate one of the products 26b-26g that is to be used next, and will do so only after a predetermined period of time has elapsed. This relieves the user of product containment system 24 from the tasks of determining what product to use next and when it might be necessary to use the product.

In this embodiment, each of products 26b-26g is to be accessed no sooner than 24 hours after a preceding one of products 26a-26f has been accessed. Accordingly, indicators 70a-70f generally maintain a first appearance until about 24 hours after exposure to ambient air 80. After a 24 hour period of exposure to ambient air 80, indicator 70a changes from a first appearance shown in FIGS. 2-9 to a second appearance shown in FIGS. 10 and 11. As is shown in FIGS. 10 and 11, indicator 70a has a second appearance that is different from the appearance of other portions of visible area 72a of film 60. This then provides an observer with an indication that it is now time to access product 26b which, in this embodiment, is the next one of products 26b-26g to be accessed in the sequence of products 26a-26g.

Similarly, when product 26b is accessed, indicator 70b is exposed to ambient air 80 and changes appearance 24 hours later to indicate that it is time to access product 26c. This process repeats in like fashion after products 26c, 26d, 26e and 26f are accessed.

There are various ways that product containment system 24 can be used to define the predetermined time between access to one of products 26a-26f and the change in appearance of an associated one of indicators 70a-70f.

In some embodiments, the type of gas sensitive material provided in each of indicators 70a-70f can be used to determine the predetermined time for each of indicators 70a-70f. For example, certain gas sensitive materials will change appearance at different times even though exposed to the same ambient air 80. Accordingly, in the embodiment of FIGS. 2-11 indicators 70a-70f can include gas sensitive materials that are known to transition from a first appearance to a second appearance after about 24 hours of exposure to one or more of the gases in ambient air 80.

Alternatively, in the embodiment of FIGS. 2-11, indicators 70a-70f can use gas sensitive materials (such as different gas sensitive materials) that transition from a first appearance to a second appearance at times that are greater than or less than 24 hours of exposure to ambient air 80 but that are treated, processed, patterned, printed, coated, overcoated or applied in ways that reduce the rate of exposure of indicators 70a-70f to gasses in ambient air; or that accelerate or delay the change in appearance of gas sensitive materials so that such gas sensitive materials cause indicators 70a-70f to transition from the first appearance to the second appearance after a predetermined period of time. For example and without limitation, the embodiment of FIGS. 2-11 can use gas sensitive materials in indicators 70a-70f that would cause indicators 70a-70f to transition from a first appearance to a second appearance in 12 hours when directly exposed to ambient air 80, where such gas sensitive materials are coated with a material that is semi-permeable to ambient air 80. Such semi-permeable material can adjust or restrict the rate at which this gas sensitive material is exposed to ambient air 80 so as to delay the change in appearance of indicators 70a-70f so that indicators 70a-70f change appearance after 24 hours after exposure to ambient air 80. Accordingly, the present invention can provide for an adjustment or modification or control of the time or rate at which the indicators 70a-70f can transition from a first appearance to a second appearance through at least the selection of the gas sensitive material or a coating applied on the gas sensitive material.

Figure 12:
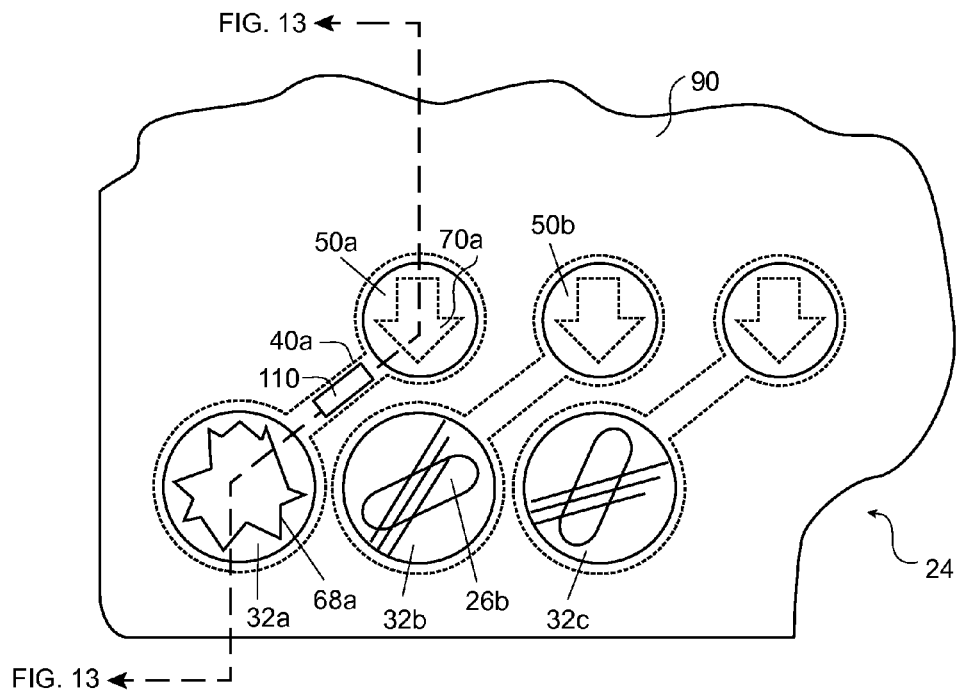
FIG. 12 is a top cutaway view of an embodiment of a product containment system having an oxygen scavenger.
Figure 13:
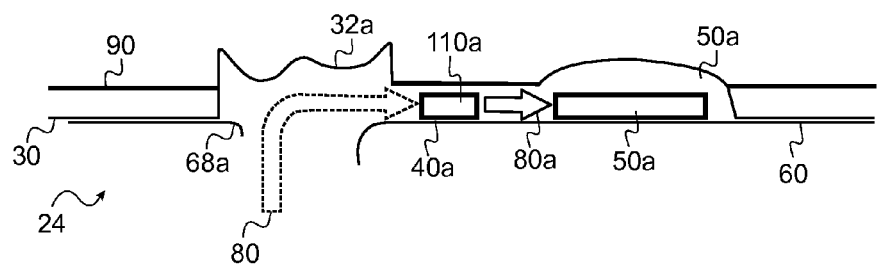
FIG. 13 is a section view of the embodiment of FIG. 12 taken as indicated in FIG. 12.

Another embodiment of a product containment system 24 is shown in FIGS. 12 and 13. The embodiment of FIGS. 12-13 is substantially similar to that shown in FIGS. 2-11 but includes the addition of a gas scavenger 110 that is positioned between a product compartment 32a that has an indicator 70a. The gas scavenger 110 is adapted to absorb one or more of the gasses in ambient air 80 that a gas reactive material in indicator 70a reacts with to cause a change in appearance of the indicator 70a. This causes the predetermined time between the creation of disruption 68a and a time of transition of indicator 70a to be longer in the embodiment of FIGS. 12 and 13 than in the embodiment of FIGS. 2-11.

In the embodiment of FIGS. 12 and 13, gas scavenger 110 comprises an oxygen scavenging material that is supplied in conduit 40a. In other embodiments, such a gas scavenger 110 can be positioned in product compartments 32a-32g, in window chambers 50a-50f (as shown in, for example, FIG. 15) or on film 60.

In any of these embodiments, the predetermined time can be adjusted or modified by controlling the intensity of the gas scavenging of the gas scavenger 110 or the capacity of gas scavenger 110 to scavenge gas(ses) from ambient air 80. These factors, in turn, can be controlled by selection of a gas scavenging material to be used in gas scavenger 110 by controlling, for example and without limitation, the amounts, the size, the shapes, the patterns or the surface area of gas scavenging materials in gas scavenger 110. Accordingly, by proper control of such factors it becomes possible to control the predetermined time between the creation of a disruption such as disruption 68a and the time at which an indicator such as indicator 70a transitions from the first appearance to the second appearance. In some examples of this embodiment, the gas scavenger 110 and the gas reactive material in indicator 70a can be the same material and in such embodiments the gas scavenging material can be positioned in locations that will not be visible to an observer of window chamber 50a because these areas are located under cover sheet 90.

As is noted above, in the embodiment of FIGS. 12 and 13, gas scavenger 110 is an oxygen scavenger. A wide variety of oxygen scavenging materials are available and can be used to form such an oxygen scavenger. These materials can include but are not limited to organic oxygen scavengers such as carbohydrazide, diethyl hydroxylamine (DEHA), methyl ethyl ketoxime (MEKO), hydroquinone, or tannin, and inorganic oxygen scavengers such as sodium sulfite and hydrazine.

Figure 14:
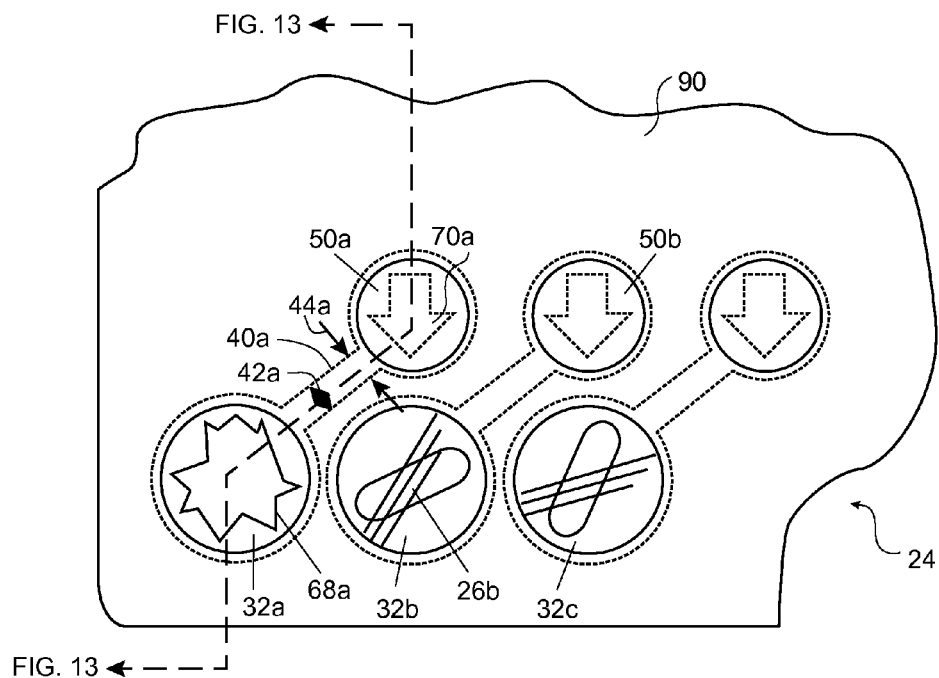
FIG. 14 is a top cutaway view of an embodiment of a product containment system having a conduit shaped to influence a predetermined time.
Figure 15:
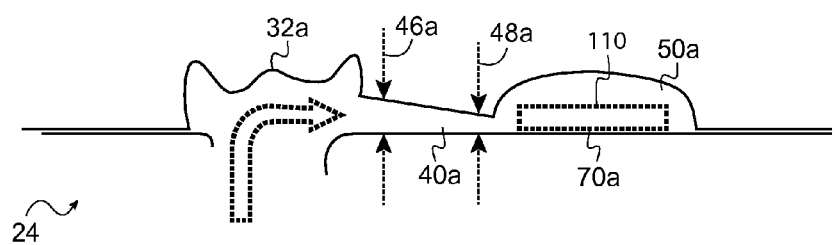
FIG. 15 is a section view of the embodiment of FIG. 14 taken as indicated in FIG. 14.

In still other embodiments, a shape, size, volume, or area of conduits 40a-40f and window chambers 50a-50f can be used to control an extent and a timing of an exposure of a particular indicator 70a-70f to gases in ambient air 80 so as to provide control over the timing of the transition of the indicator 70a-70f from the first appearance to the second appearance. For example, FIG. 14 shows a top view of a cutaway of one embodiment of a product containment system 24 having a conduit 40a with a first width 42a that tapers to a second width 44a, while FIG. 15, shows a section view of a product containment system 24 of FIG. 12 having a conduit 40a that has a first height 46a at a first position and a second height 48a at a second position between product compartment 32a and window chamber 50a; with the second height 48a being smaller than the first height 46a. It will be appreciated that this approach reduces a flow of ambient air 80 into window chamber 50a. This shapes conduit 40a to have a greater resistance to the movement of ambient air 80 than conduit 40b given that conduit 40b is not illustrated with such features. This therefore increases the amount of time required for indicator 70b to change from a first appearance to a second appearance after product 26b is accessed by removing product 26b from product compartment 32b, as compared to the amount of time required for indicator 70a to change from a first appearance to a second appearance following access of product 26a.

It will be appreciated that size and shape modifications can be made to limit the rate at which ambient air 80 can flow from disruption 68a to window chamber 50a, that such modifications can include modifications to product compartments 32a-32g, to conduits 40a-40f, to window chambers 50a-50f, and that other known methods for shaping and sizing air conduits or chambers can be used to provide controlled airflow, so as to control an amount of time between access to a product 26a-26g in a product compartment 32a-32g, and a time at which an indicator 70a-70f that is in a window chamber 50a-50f that is connected to the holding chamber changes appearance.

It is not necessary that indicators 70a-70f each change from a first appearance to a second appearance at the same time following exposure to ambient air 80. For example, an amount of time between an exposure of indicator 70a to ambient air 80, and a time at which indicator 70a changes from the first appearance to the second appearance can be significantly longer or shorter than an amount of time between an exposure of indicator 70b to ambient air 80, and a time at which indicator 70b changes from a first appearance to a second appearance. In this regard, the various techniques described above for controlling the time at which a particular indicator transitions from a first appearance to a second appearance can be used in different ways to cause, for example, indicator 70a to transition from the first appearance to the second appearance fifteen minutes after product 26a is accessed, while causing indicator 70b to transition from the first appearance to the second appearance 24 hours after second product 26b is accessed. These examples are non-limiting.

It will be appreciated from this that by using product containment system 24 to package products 26a-26g it becomes possible to form a product containment system 24 with accurate indications of the sequence and relative times at which products 26a-26g are to be used. Additionally, it will be appreciated that the use of conduits 40a-40f to separate product compartments 32a-32g from indicators 70a-70f enables product containment system 24 to have products 26a-26g without requiring that products 26a-26g be arranged in a positional sequence and without requiring special attention to product instructions and labeling.

Figure 16:
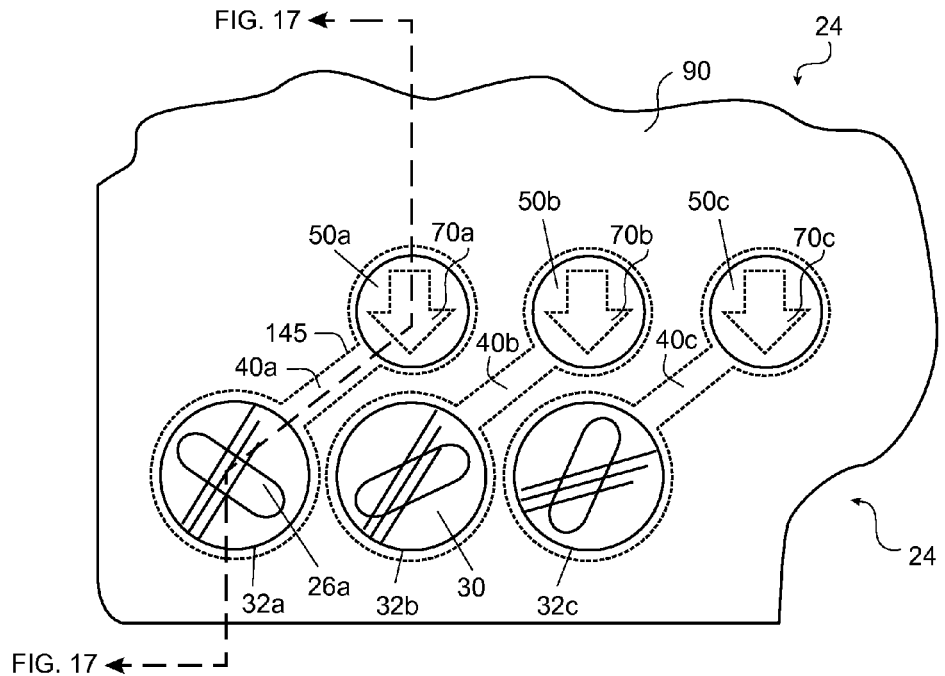
FIG. 16 is a cutaway view of an embodiment of a containment system having an oxygen scavenger.
Figure 17:
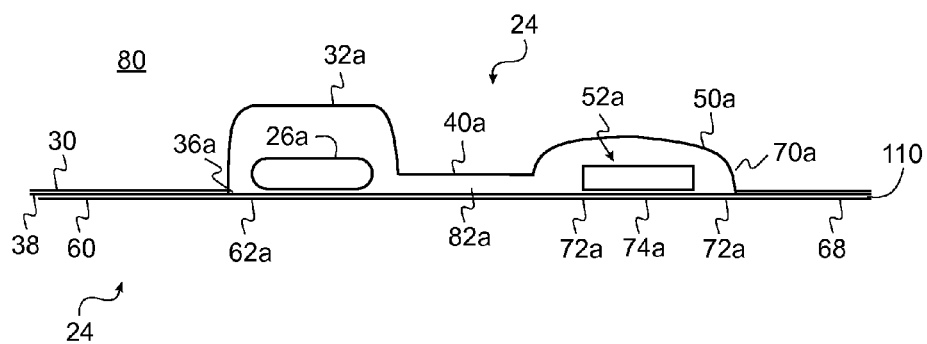
FIG. 17 is a section view of the embodiment of FIG. 16 taken as indicated in FIG. 16.

FIGS. 16 and 17 shows still another embodiment of a product containment system 24 in accordance with the present invention. In this embodiment, product containment system 24 has a gas scavenger 110' (FIG. 17) between film 60 and substrate 30. In this embodiment, the gas scavenging material is applied as a layer on a surface of film 60 that confronts substrate 30 when film 60 is bound to substrate 30. In this embodiment gas scavenger 110' further isolates product compartments 32a-32g, conduits 40a-40f and window chambers 50a-50f from gasses in ambient air 80 in areas between product compartments 32a-32g, conduits 40a-40f and window chambers 50a-50f. In this embodiment, gas scavenger 110' can be printed, coated or otherwise bonded to substrate 30 or to film 60 prior to assembly of product containment system 24. Such printing or coating can be patterned or uniform. Gas scavenger 110' can also be provided in a matrix or mixed with adhesives or other bonding agents that help to bond and form seals between substrate 30 and receive 24.

Optionally gas scavenger 110 or 110' can be provided in product compartments 32a-32g, conduits 40a-40f and window chambers 50a-50f (for example, see FIG. 15) to reduce the extent to which any gases in product compartments 32a-32g, conduits 40a-40f and window chambers 50a-50f during manufacture of product containment system 24 can react with gas sensitive materials in indicators 70a-70f after manufacture but prior to a time at which any of products 26a-26g are accessed. Further, the presence of such gas scavenger 110 or 110' in product compartments 32a-32g, conduits 40a-40f and window chambers 50a-50f can also help to control the extent and timing of exposure of gas sensitive materials in indicators 70a-70f so as to help control when indicators 70a-70f transition from a first appearance to a second appearance following access of a product contained in one of product compartments 32a-32g as is generally described above.

A wide variety of gas scavenging materials are known that can be used to form a gas scavenger 110, 110'. For example, oxygen-scavenging material such as those that are described in U.S. Pat. Pub. 2006/0110835A1 "Apparatus For Indicating The Passage Of Time And Method Therefor and Articles Therewith". U.S. Pat. Pub. 2006/0110835A1 describes using an oxygen scavenging material to delay or control the elapsed time interval causing a reduction-oxidation (redox) dye to change color. This approach is also limited to one individual fixed time interval and does not provide an indication of a sequence of individual fixed or variable timed events.

As is described in U.S. Pat. Pub. 2006/0110835A1, suitable oxygen-scavenging materials include the oxygen-indicating tablets sold by Mitsubishi Chemical Company under the trademark, "Ageless®", such as Ageless® E-200 oxygen-indicating tablets. The ultraviolet light activatable polymeric oxygen-scavenging system sold by Cryovac Company as Cryovac OS2000 system, or the ultraviolet light activatable formulation described in PCT published application WO 2004/005424, may also be used. Other suitable oxygen-scavenging materials include tannin, carbohydrazide and the material sold by Completion Products and Services as OS-8, an organic salt that is a non-sulfur-based oxygen scavenger. An ultraviolet light activatable material may be preferred as it offers the advantage of longer shelf life for a time-indicating apparatus because it removes the necessity of storage of the time-indicating apparatus in a non-oxygen environment. Other commercially available oxygen scavenging materials such as oxygen-scavenging additives sold under the brand name of O2Block by NanoBioMatters Industries S.L., Valencia, Spain, can be dispersed directly into the packaging materials. This material is based on surface-modified phyllosilicate clay that is functionalized with active iron to create a naturally sourced and highly efficient oxygen scavenging product.

As noted above, indicators 70*a*-70*f* include gas reactive materials that cause indictors 70*a*-70*f* to change from a first appearance to a second appearance after an exposure to one or more gasses in ambient air 80. Examples of such gas reactive materials include, those described in U.S. Pat. Pub. 2011/0139655A1 "Indicating Package" which describes an ink, that shows whether the inside of a package has been exposed to air and hence oxygen, by a color change or response to an external stimulus. Similarly, U.S. Pat. Pub. 2010/0221468A1 "Printable Oxygen Sensing Composition" describes an oxygen sensing composition capable of being printed by a variety of printing techniques and that can be used to cause a change in an appearance of an indicator after a period of exposure time to oxygen. U.S. Pat. Pub. 2010/0221468A1 discloses the use of fluorescing dyes for this purpose. As is noted therein, the dye should be capable of fluorescing in a manner proportional to the oxygen content of the atmosphere surrounding it. Thus, for example, the intensity of fluorescence may be proportional to oxygen content, or, and more preferably, the decay of fluorescence may be proportional to oxygen content, as in the prior art. Examples of such dyes include: ruthenium (II), osmium(II), iridium(III), rhodium(III) and chromium ions with ligands, especially alpha-diimine ligands, such as 2,2'-bipyridine, 1,10-phenanthroline, 4,7-diphenyl-1-10-phenanthroline, 4,7-disulphonated-diphenyl-1,10-phenanthroline, 5-bromo-1,10-phenanthroline, 5-chloro-1,10-phenanthroline and other diimine ligands. Examples of these complexes include tris(2,2'-bipyridine)ruthenium(II) salts, tris(1,10-phenanthroline)ruthenium(II) salts and tris(4,7-diphenyl-1-10-phenanthroline)ruthenium (II) salts, especially the chloride described above. Other possible systems include similar palladium(II) and platinum(II) complexes with alpha-diimine ligands. Of these dyes, the tris(4,7-diphenyl-1-10-phenanthroline)ruthenium (II) salts, especially the chloride is preferred. One or more of these dyes is then immobilized in a polymer matrix having pendant sulphonic or phosphonic groups (the term "sulphonic groups" being used herein to mean sulphonic acid groups or ester or salt groups derived from such sulphonic acid groups and the term "phosphonic groups" being used correspondingly to mean phosphonic acid groups or ester or salt groups derived from such phosphonic acid groups). The polymer used in the present invention may be prepared by copolymerising a first ethylenically unsaturated compound, e.g. an acrylic monomer or oligomer, with a second ethylenically unsaturated compound, this one containing one or more sulphonic or phosphonic groups. Provided the acrylic monomer or oligomer and the sulphonic or phosphonic group-containing compound are copolymerisable, there is no particular restriction on them. U.S. Pat Pub. 2006/0110835A1 also describes the use of dyes that undergo a reduction-oxidation (redox) dye to change color. Examples of such dyes include leucomethylene blue, indigo carmine, Ciba Scarlet B. G., Cibanone Yellow, sodium anthraquinone beta-sulfonate, may be used. The weight of the reduced redox dye disposed in the receptacle having a surface area of approximately four square inches (4 in.sup.2; 6.45 cm.sup.2) is preferably in the range from 0.025 mg to 200 mg, and more preferably in the range from 0.025 mg to 1 mg. U.S. Pat Pub. 2006/0110835A1 also cites a Cibanone Yellow dye as a preferred redox dye. The reduced form of this dye gives a perceived initial color as intense blue or red-orange (depending upon the ratio of the components of the preferred reducing agent, to be discussed). The perceived final color of the oxidized form of this dye is yellow. This approach is also limited to one individual fixed time interval and does not provide an indication of a sequence of individual fixed or variable timed events.

Other examples include materials prepared by Andrew Mills, as described in the article, "Oxygen indicators and intelligent inks for packaging food", The Royal Society of Chemistry, 2005, Chemical Society Reviews, Chapter 34, Pages 1003-1011, who has developed an irreversible solvent-based blue ink, which upon activation with UV light, loses all its color and becomes oxygen sensitive; it will only gain its original color upon exposure to oxygen.

An advantage of the oxygen ink over most of the traditional methods for detecting oxygen are that it is cheap and easy to use, especially as it relies on a color-change detectable by the human eye. Solvent-based inks such as these may also be easier to print on the common polymers used in food packaging. Other examples of materials can be found in: A. Mills, C. Thommons, R. Bailey, M. C. Tedford Crilly, "UV-Activated Luminescence/Colourmetiric O2 Indicator" International Journal of Photoenergy, Article ID 547301, 2008, S-K. Lee, A. Mills and A. Lepre "An intelligence ink for oxygen," Chemical Communications, No. 17, pp. 1912-1913.

Figure 18:
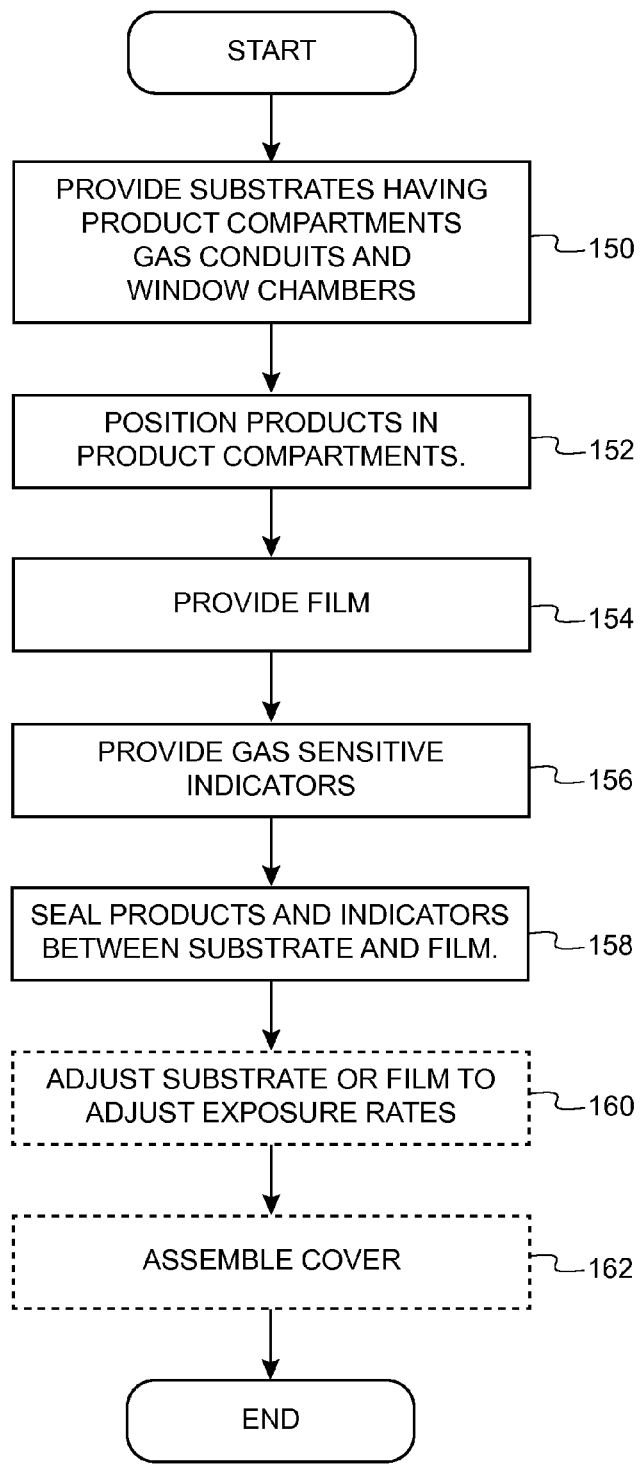
FIG. 18 shows a first embodiment of a method for manufacturing a product containment system in accordance with the present invention.
Figure 19:
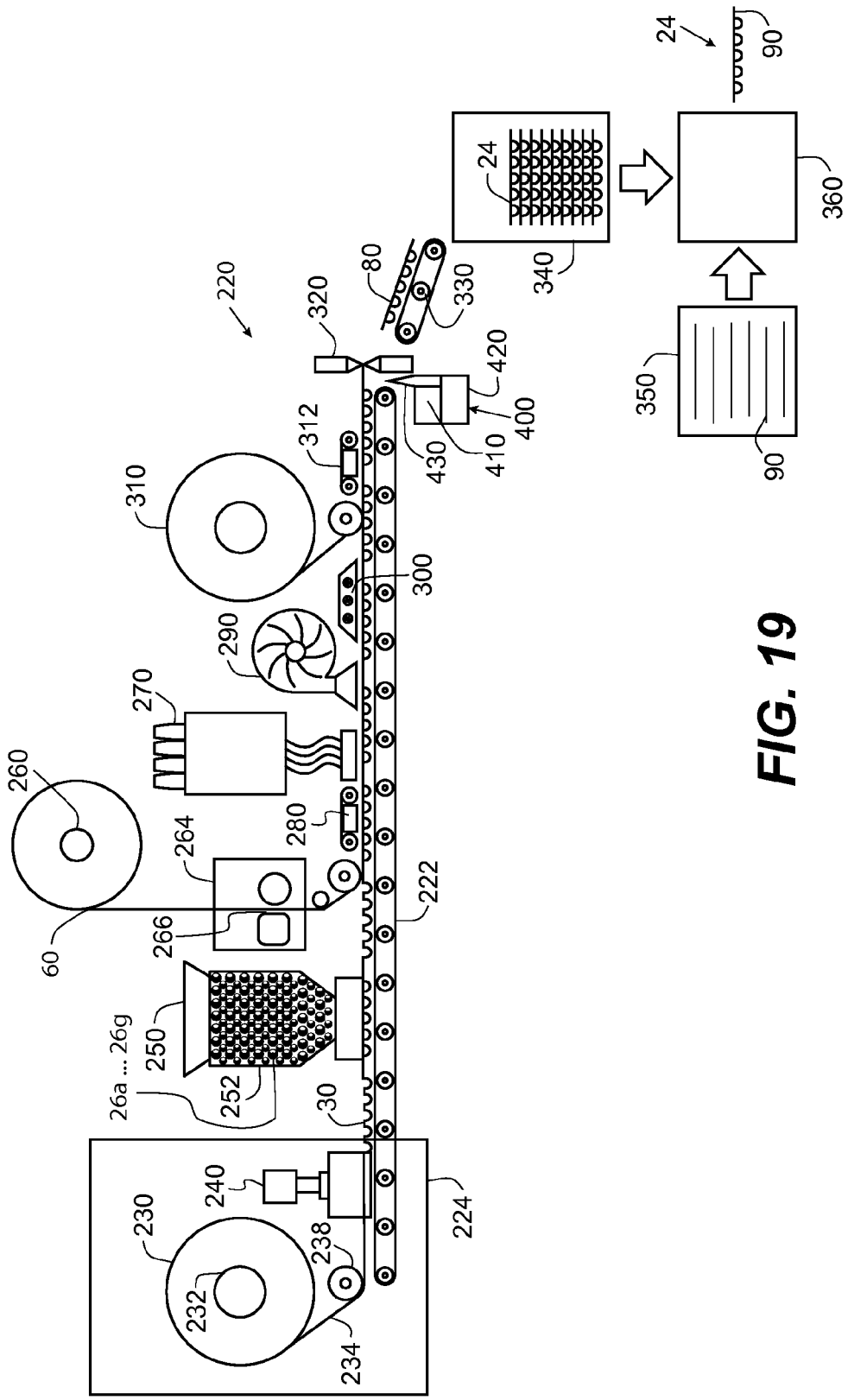
FIG. 19 shows a first embodiment of an apparatus for manufacturing a product containment system in accordance with the present invention.
Figure 20:
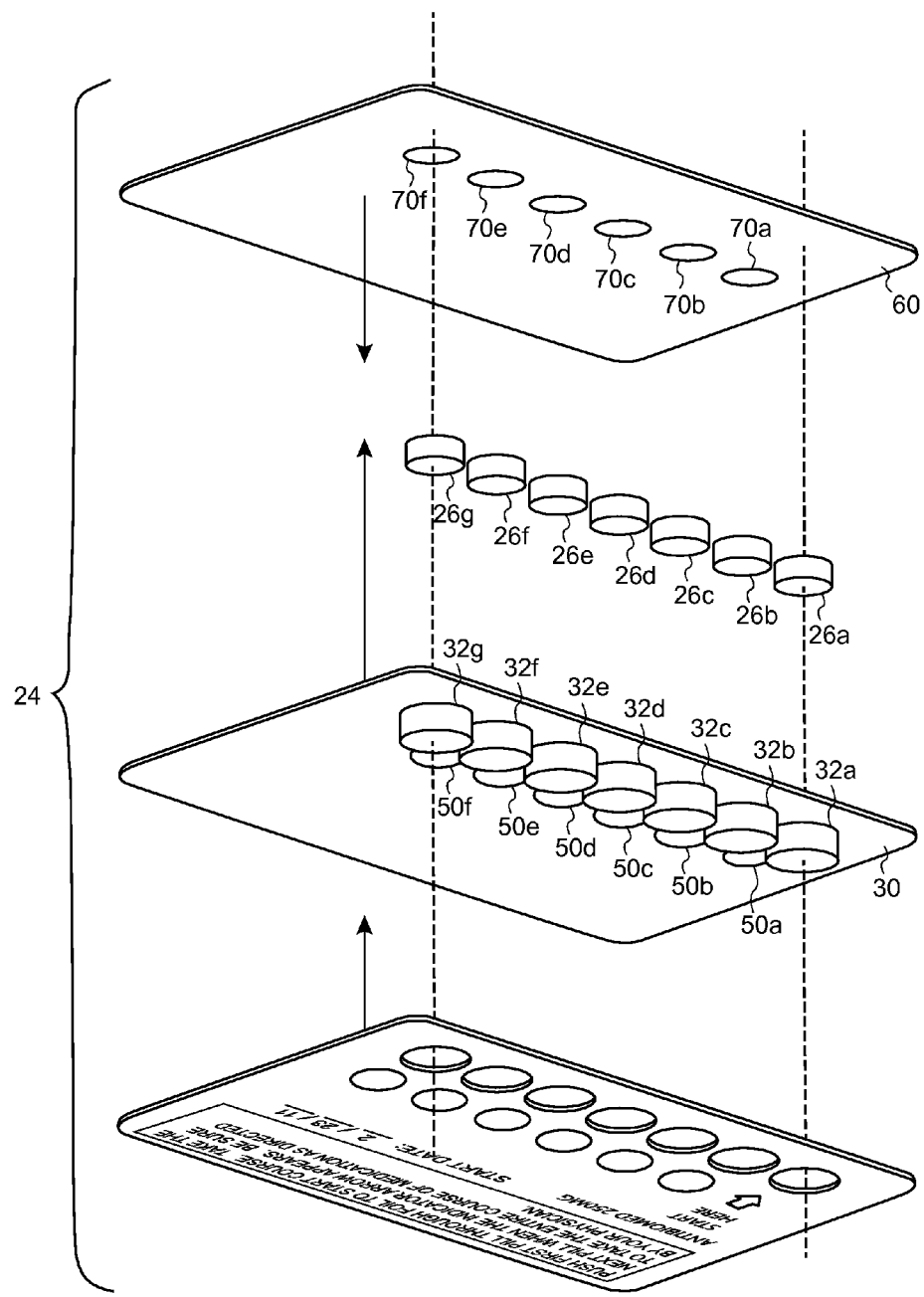
FIG. 20 shows an assembly view of a product containment system in accordance with the present invention.

FIG. 18 illustrates one embodiment of a method for manufacturing a product containment system 24 in accordance with the present invention. FIG. 19 illustrates one embodiment of a product containment system manufacturing line 220 in accordance with the present invention that can be used to manufacture a product containment system 24 and that can be used, for example, in the performance of the method of FIG. 18. FIG. 20 provides an assembly view of one embodiment of a product containment system 24 made according the method of FIG. 18 using the product containment system manufacturing line 220 of FIG. 19.

According to the method of FIG. 18 (step 150), a substrate 30 is provided having a plurality of product compartments 32*a*-32*g* each with a volume sufficient to receive at least one of a plurality of products 26*a*-26*g*, with a plurality of gas conduits 40a-40f each leading from one of product compartments 32a-32g to one of a plurality of window chambers 50a-50f. Window chambers 50a-50f each have a window volume. The provided substrate 30 can take the form of any embodiment having such features. For convenience only, the embodiments described with reference to FIGS. 18, 19, and 20 will be described as using the embodiment of substrate 30 illustrated in FIGS. 2-11. Accordingly, as is illustrated in FIG. 20 and described above, in this embodiment, substrate 30 has a plurality of product compartments 32a-32g, a plurality of window chambers 50a-50f and a plurality of conduits 40a-40f (not shown in FIG. 20) that connect individual ones of product compartments 32a-32g to respective ones of window chambers 50a-50f as is described and shown above in greater detail with reference to FIG. 2-11.

Substrate 30 can be provided in a variety of ways, such as by fabrication, assembly or other known techniques for forming a substrate 30 or by positioning prefabricated or preassembled substrates for use in forming a product containment system 24.

The embodiment of product containment system manufacturing line 220 shown in FIG. 19 illustrates one example of one way in which a substrate 30 can be provided. In this embodiment, product containment system manufacturing line 220 has a powered conveyor 222 and a source of substrates 224 that supplies substrates 30 to powered conveyor 222. In this embodiment source of substrates 224 comprises a supply 230 of a formable film 234 and a molding station 240. In this embodiment, formable film 234 is thermally formable and is supplied in the form of a continuous web that is wound and stored on roller 232 and drawn therefrom as needed. Examples of such thermally formable films can include but are not limited to polymeric and other organic plastic films such as polyesters and polystyrenes. Formable film 234 is then guided though an optional pre-heating station shown here as heated roller 238 and is then supplied to molding station 240.

In this embodiment, molding station 240 thermoforms and optionally sizes formable film 234 using conventional techniques for hot molding such as by using a heated two-part form or using a vacuum-forming device to form product compartments 32a-32g, window chambers 50a-50f and gas conduits 40a-40f as is described in greater detail elsewhere herein. Examples of a thermally formable film 234 include polyvinyl chloride (PVC) which has excellent thermoforming and optical transparency properties and is used to provide the basic structure of the thermoformed blister pack tray, but is a poor barrier against moisture and oxygen. PVC can be combined with other materials via co-extrusion or lamination to form multi-layer bather films. For example, PVC can be laminated to polychlorotrifluoro ethylene (PCTFE) to obtain an oxygen and moisture barrier. In addition, PVC can be coated with polyvinylidene chloride (PVDC) known by the trade name "Saran" or laminated to PCTFE or cyclic olefin copolymers (COC) to increase the barrier properties.

In one embodiment, ultraviolet (UV) light can be provided to the gas sensitive indicators 70a-70f by way of window chambers 50a-50f during production of product containment system 24. This UV light can be used to make gas sensitive materials in indicators 70a-70f become reactive to gasses in ambient air 80 so that predetermined times between exposure of indicators 70a-70f to ambient air 80 after products 26a-26g are accessed are maintained despite any exposures. Alternatively, indicators 70a-70f can be provided with a temporary barrier to exposure to ambient air to prevent reaction of indicators 70a-70f during assembly of product containment system 24.

In other embodiments, formable film 234 can comprise a cold formable film such as an aluminum-based laminate film that can be cold stamped or drawn to form substrates 30 having the desired arrangement of product compartment 32a-32g, window chambers 50a-50f and gas conduits 40a-40f as is generally described above under certain circumstances. The use of a cold formable film 234 of this type can provide a highly effective barrier against water and oxygen but lacks the transparency of thermoformed plastics.

Products 26a-26g are positioned in product compartments 32a-32g (step 152). Product containment system manufacturing line 220 illustrates one, non-limiting method for positioning products 26a-26g in product compartments 32a-32g. As is shown in the embodiment of FIG. 19, a product dispenser 250 distributes products 26a-26g from a dispenser supply 252. A variety of conventional sources of product dispensers can be used for this purpose. In this embodiment, product dispenser 250 takes the form of a bulk dispenser of products 26a-26g. As shown in the example, the same product 26a-26g is used in each of product compartment 32a-32g. However, where more than one different type of product 26a-26g is loaded into each of product compartments 32a-32g, more complex dispensing equipment can be used. For example, pick and place robotic or other forms of automatic assembly equipment known in the art can be used for this purpose. Additionally, dedicated dispensing tooling adapted to deliver different products can also be used to enable high-volume production of product containment system 24.

Film 60 is then provided (step 154). There are a number of ways in which film 60 can be provided. In the embodiment shown in FIG. 19, film 60 is supplied in the form of a continuous web that is stored on a spool 260 and supplied as needed. In other embodiments, film 60 can be provided in other convenient forms including sheet forms.

Gas sensitive indicators 70a-70f are provided in areas that will be aligned with window chambers 50a-50f after film 60 is joined to the substrate 30 (step 156). In the embodiment of FIGS. 18-20, indicators 70a-70f are shown being provided on film 60. In this regard, an indicator application system 264 prints, transfers, adheres or otherwise applies materials forming gas sensitive indicators 70a-70f to film 60. In this embodiment, indicator application system 264 has a printhead 266 that prints indicators 70a-70f on a surface of film 60 that confronts substrate 30. Printhead 266 can comprise, for example and without limitation, an inkjet printhead, a thermal printhead, an electrophotographic printhead, or a contact printing plate or system. In other embodiments, indicator application system 264 can comprise a system for transferring a structure such as a film, fabric or sticker to film 60.

Substrate 30 and film 60 are sealed together with products 26a-26g and gas sensitive indicators 70a-70f therebetween and with gas sensitive indicators 70a-70f aligned with window chambers 50a-50f so that the appearance of gas sensitive indicators 70a-70f can be observed through window chambers 50a-50f (step 158). This encapsulates indicators 70a-70f between substrate 30 and film 60 to isolate indicators 70a-70f from ambient air 80. In addition, in other embodiments window chambers 50a-50f can allow ultraviolet or other light to pass through substrate 30 to the gas sensitive indicators 70a-70f during production of the Push-Through-Packs on a blisterline to initiate the gas sensitive reaction where indicators 70a-70f require such exposure.

In the embodiment of FIG. 19, a film application system 280 is used to apply film 60 to form gas seals for each of the product compartments 32a-32g and any associated ones of conduits 40a-40f and window chambers 50a-50f. Film 60 can be bound to substrate 30 using pressure and heat to weld, bond or fuse or otherwise form a seal between substrate 30 and film 60. In the embodiment that is illustrated, film application system 280 applies heat and pressure to film 60 to form a bond between film 60 and substrate 30 that sealing encloses each of product compartments 32a-32g, any associated conduits 40a-40f and window chambers 50a-50f.

In the embodiment of FIG. 19, product containment system manufacturing line 220 has indicator application system 264 and film application system 280 closely positioned to limit the amount of time that film 60, and indicators 70a-70f thereon are exposed to ambient air 80 before indicators 70a-70f are enclosed between substrate 30 and film 60. In other embodiments, product containment system manufacturing line 220 can be operated in an environment that has low concentrations of gasses in ambient air 80 to which gas sensitive materials in indicators 70a-70f react. This can be done, for example, by providing a low pressure atmosphere around film 60 between printing of indicators 70a-70f and sealing assembling film 60 to substrate 30 in areas between the provision of indicators 70a-70f on film 60 and the joining of film 60 to substrate 30. This can also be done by creating an increased concentration of gasses that do not interact with gas sensitive materials in indicators 70a-70f.

A printing system 270 prints text, graphics and other information on film 60 and a dryer 290 directs heat or airflow at film 60 when printing by printing system 270 involves the use of types of printing that require drying.

One or more additional films 310 can also be supplied for purposes such as protecting printing made on film 60, enhancing the gas bather capabilities of film 60, or for aesthetic reasons. Film 310 is then bonded to film 60 using a bonding system 312 that creates such a bond using heat and pressure or other activating energies to induce bonding of film 310 to film 60.

After assembly, substrate 30, film 60 and optionally film 310 are then measured and cut by an inline cutter 320 and advanced by an output conveyor 330 to a collection bin 340.

Optionally, a cover sheet 90 can be supplied and joined thereto (step 162). Cover sheet 90 can be created using conventional printing and cutting systems 350 including but not limited to conventional printers such as inkjet printers, electrophotographic printers, other toner printers, and contact printers and conventional paper punch or laser cutting systems. Sheets 90 can be joined to substrate 30 using conventional assembly and bonding equipment 360 that receives assembled product containment systems 24 and adds optional cover sheets 90. Conventional positioning systems such as conveyors and other known material handling techniques can be used to position product containment systems 24 and cover sheets 90 relative to each other. Similarly, assembly bonding equipment 360 can include adhesive applicators or activators or thermal systems that can cause heat bonding of cover sheet 90 to substrate 30.

Also shown in FIG. 18 (Step 160) is an optional adjustment step, in which substrate 30 or film 60 are resized to adjust exposure rates of at least one of the indicators 70a-70f. FIG. 19 shows one embodiment of an optional resizing system 400 that can be used to resize substrate 30 for such a purpose. In this embodiment, resizing system 400 comprises a shaping element such as a hot or cold form that can be used to resize any of conduits 40a-40f or window chambers 50a-50f in order to control a rate at which ambient air 80 can flow to indicators 70a-70f located in such window chambers 50a-50f. This allows a source of substrates 30 to supply substrates 30 having uniformly shaped conduits 40a-40f and/or window chambers 50a-50f while still allowing the substrates to provide different predetermined delays between a time at which gas seals associated with different ones of a sequence of products are disrupted, and a time at which indicators for the next product are to change appearance. That is, a uniform substrate 30 can be provided that can be modified to provide different predetermined delays for different ones of products assembled thereto. Such modifications can occur after manufacture.

In one embodiment, where substrate 30 comprises a heat formable film, optional resizing system 400 uses a heater 410 and an actuator 420 to advance a surface 430 into contact with one or more of conduits 40a-40f of substrate 30 to adjust the shape of a conduit 40a-40f to provide a controlled resistance to ambient air flow into individual ones of viewing chambers 50a-50f. By causing different ones of conduits 40a-40f to have different resistances to the flow of ambient air 80 into different viewing chambers 50a-50f, each of indicators 70a-70f can be made to have a different rate of exposure to ambient air 80 and therefore to change appearance at different times. This can be done, for example, by modifying a substrate 30 having identically sized and shaped conduits 40a-40f so that, for example, one of conduits 40a-40f has a different size or shape as is discussed above in greater detail with respect to FIGS. 14 and 15. It will be appreciated that where film 60 can reliably retain a modified shape, resizing system 400 can be repositioned to modify film 60 in the area of one or more conduits 40a-40f or window chambers 50a-50f to create increased resistance to flow in like fashion with similar results.

If cover sheet 90 is made of paper board, card board, or the like, or is otherwise opaque it is provided with cover sheet apertures 94a-94f (FIG. 2) that are aligned with each of window chambers 50a-50f so that visible areas 72a-72f can be observed.

Figure 21:
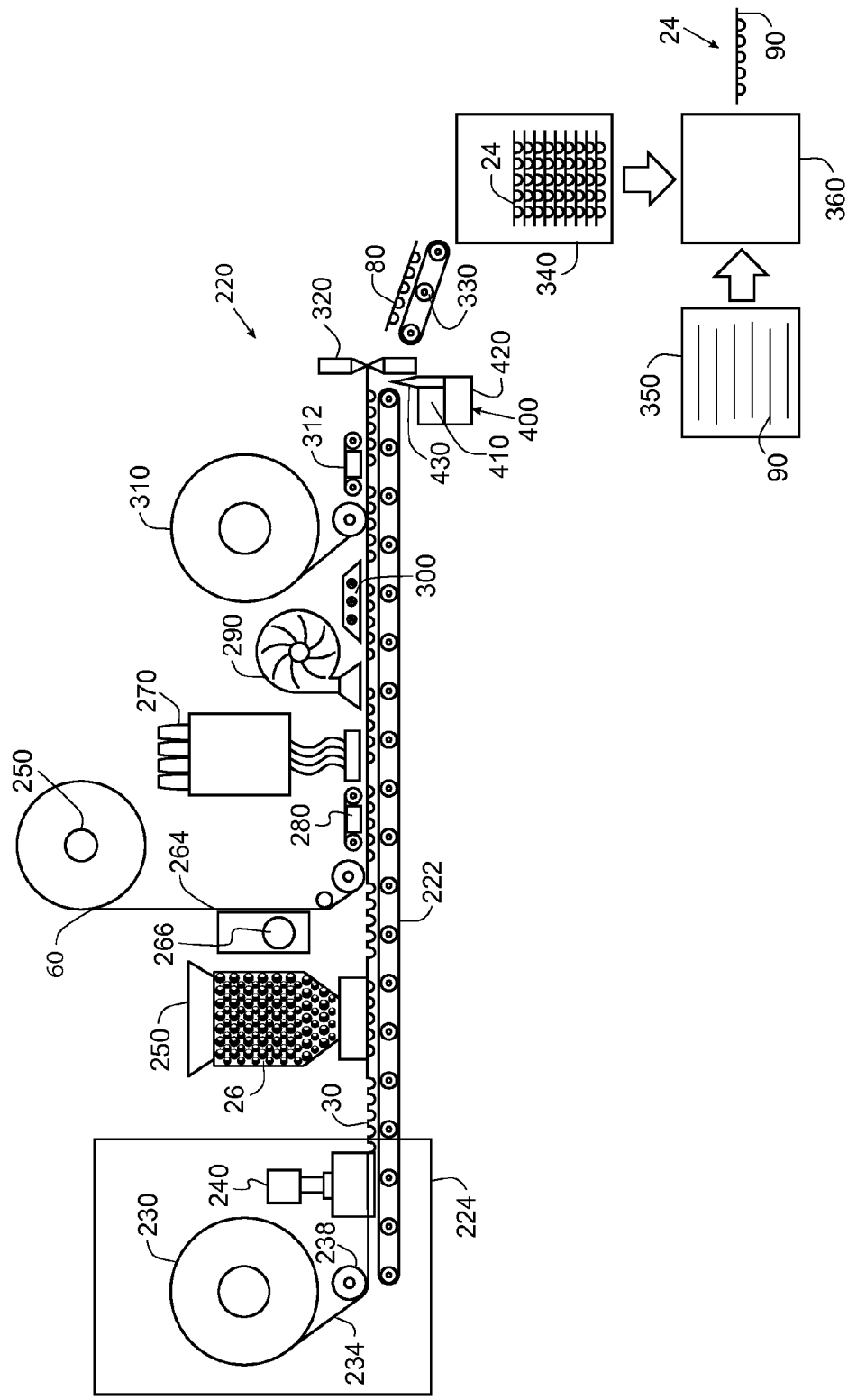
FIG. 21 shows another embodiment of a product containment system assembly line in accordance with the present invention.
Figure 22:
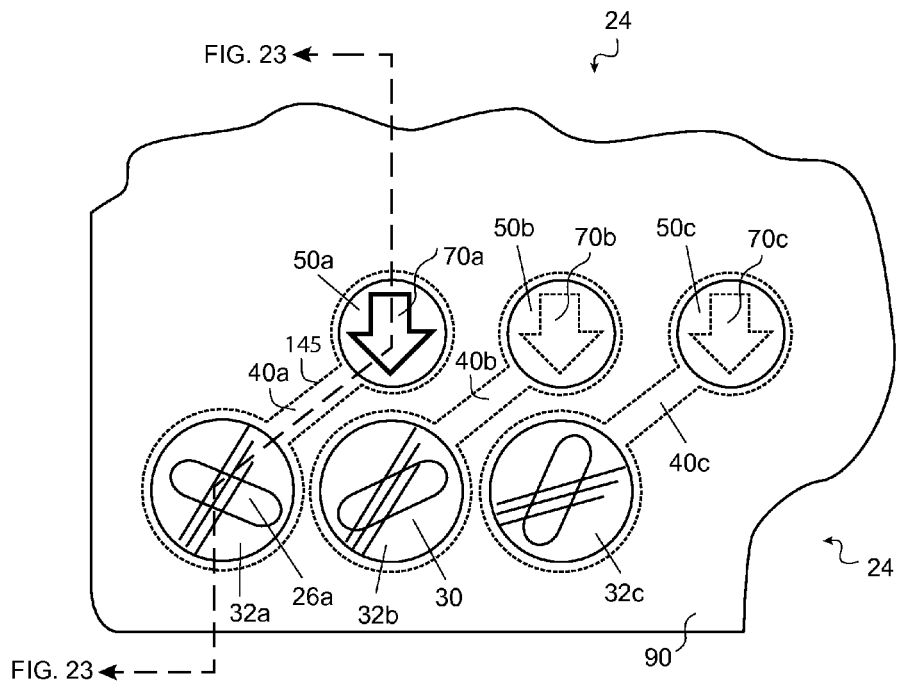
FIG. 22 shows a cut away view of another embodiment of a product containment system in accordance with the present invention.
Figure 23:
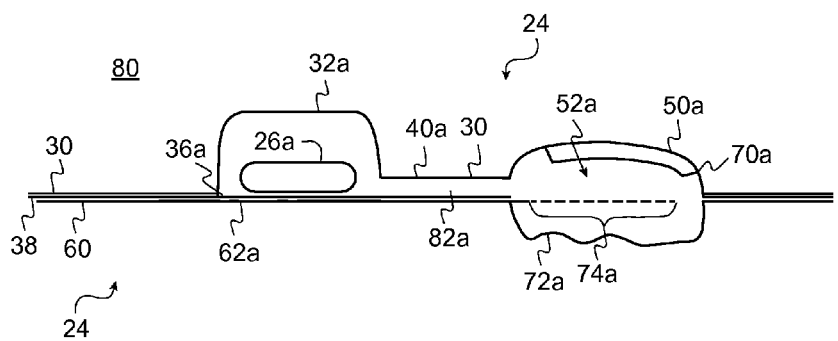
FIG. 23 shows a section view of the embodiment of FIG. 22 taken as indicated in FIG. 22.

In other embodiments, indicators 70a-70f can be printed on substrate 30 against window chambers 50a-50f. For example, FIG. 21 illustrates an embodiment of a product containment system manufacturing line 220 having an indicator application system 264 that is positioned proximate to substrate 30 to apply indicators 70a-70f directly to substrate 30 and that does so in window chambers 50a-50f. FIGS. 22 and 23 illustrate a cut away view of one example of such an arrangement of a product containment system 24. As can be seen here, indicator 70a is formed in an indicating portion 74a that is within a visible area 72a that can be observed through window chamber 50a.

In another alternative embodiment, gas sensitive indicators 70a-70f are printed on substrate 30 by replacing the paper board cover sheet 90 with a mounting card made of a transparent gas barrier material like the product tray and sealed to the top surface of the substrate 30. Ink printing and/or additional labels can be used to obscure portions of the top surface, provide text and/or graphics, and to provide instructions. The third position in the sequence is shown with un-deployed gas sensitive indicator 70a-70f, which will become visible through aperture 94 and window chamber 50a after a predetermined amount of time after the product 26a in product compartment 32a has been removed by disrupting the gas seal 62.

Figure 24:
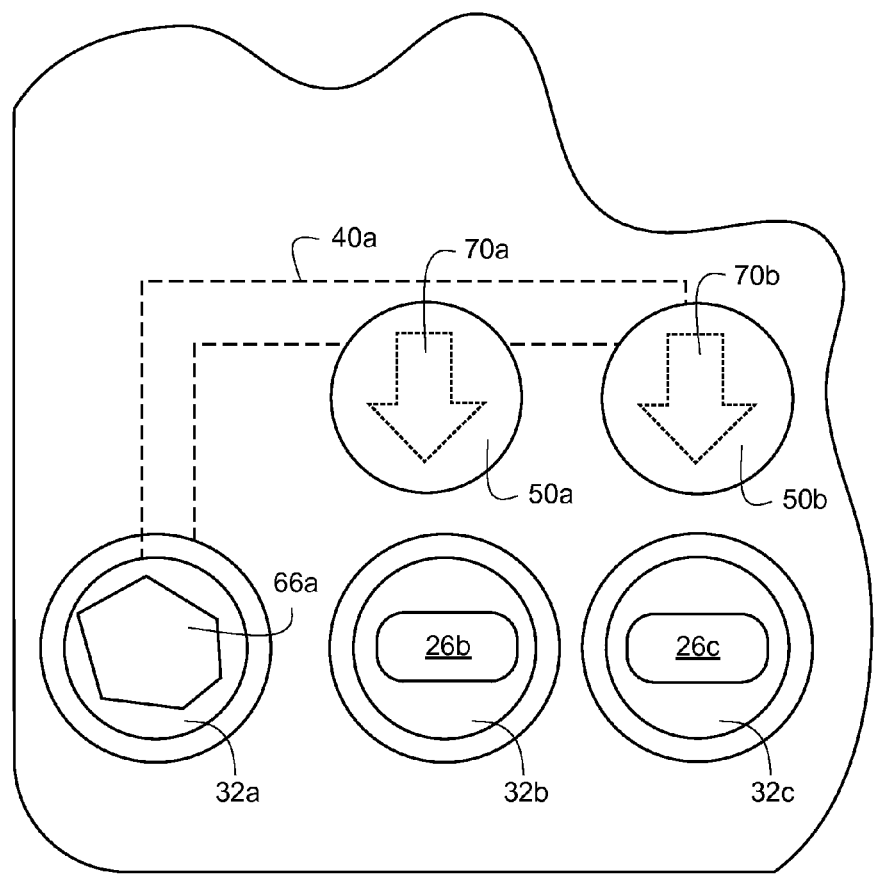
FIG. 24 shows a cut away of another embodiment of a product containment system in accordance with the present invention in which two indicators have an appearance indicating that it is time to use two different products.

FIG. 24 is a cut away view of another embodiment of a product containment system 24. FIG. 24 illustrates a product containment system 24 after a product (not shown) in product compartment 32a has been removed creating a disruption 66a that allows ambient air 80 into a conduit 40a (shown in phantom) that is linked to a window chamber 50a and a window chamber 50b. FIG. 24 illustrates this embodiment of product containment system 24 at or after a predetermined period of time when both of products 26b and 26c are to be accessed and at which indicators 70a and 70b have a second appearance indicating that it is time to access products 26b and 26c.

In a feature of the invention it is understood that gasses such as hydrogen can be found in ambient air 80 and that it is both difficult and expensive to seal against penetration of hydrogen. However, hydrogen is comprises a very small component of ambient air 80 and may not have a meaningful reaction with any of the gas reactive materials used to form indicators 70a-70f. Accordingly, a seal against ambient air 80 provided by or between substrate 30 and film 60 may not be completely impervious to all atmospheric gases while still functioning in accordance with this or other embodiments described herein.

In other embodiments, the use of conduits 40a-40f can also enable product containment system 24 to have physical arrangements of products 26a-26g that are not sequential while linking individual product compartments 32a-32f to indicators 70a-70f that are not immediately proximate to product compartments 32a-32f to which they are linked.

The invention has been described in detail with particular reference to certain preferred embodiments thereof, but it will be understood that variations and modifications can be effected within the spirit and scope of the invention.

What is claimed is:

1. A containment system for a plurality of products that are to be accessed in a predetermined timed sequence, the containment system comprising:
    a substrate with a plurality of product compartments, each of said product compartments having a volume sufficient to receive at least one of a plurality of products, said substrate further including a plurality of atmospheric gas conduits each leading from one of the product compartments to a gas sensitive indicator window chamber;
    a plurality of gas sensitive indicators having a gas reactive material that changes appearance at a predetermined time after exposure to ambient air, said gas sensitive indicators being located within a gas sensitive indicator window chamber; and
    a plurality of gas seals each sealing one of the plurality of the product compartments against atmospheric gases so that disrupting the gas seal to access a product in the product compartment allows atmospheric gas to enter the product compartment and from there to flow through one of the plurality of atmospheric gas conduits to expose at least one of the gas sensitive indicators, the one gas sensitive indicator exposed to ambient air being arranged to change appearance in a manner that indicates at least one next product in the predetermined sequence to be accessed after the predetermined time after exposure has elapsed.

2. The containment system of claim 1, wherein the predetermined time after exposure is substantially consistent for all of the gas sensitive indicators.

3. The containment system of claim 1, wherein at least two of the gas sensitive indicators have at least one of a different material, a different coating or a different pattern of application to cause the predetermined time after exposure for at least two of indicators to be different.

4. The containment system of claim 1, wherein at least one of the conduits has at least one of a different size and a different shape than the other conduits to create resistance in a flow of the ambient air from one of the product compartments to which said at least one conduit is connected to one of the window chambers to which the at least one conduit is connected to cause the predetermined time for at least one of the indicators to be different.

5. The containment system of claim 1, further comprising an oxygen scavenger between at least one of the product compartments and one of the indicators in one of the window chambers that is linked to the at least one product compartment to reduce the rate at which the one of the indicators is exposed to ambient air so as to extend the predetermined time.

6. The containment system of claim 1, wherein the gas reactive material is activatable to become gas sensitive after exposure to ultraviolet light, and wherein the window chamber allows sufficient ultraviolet light to pass through to the gas reactive material to allow the gas reactive material to be made gas sensitive.

7. The containment system according to claim 1, wherein at least one of said gas sensitive indicators further includes a semi-permeable material coated on said gas reactive material to adjust the time at which the gas reactive material changes appearance after exposure to ambient air.

8. The containment system according to claim 1, wherein at least one of a type of the gas reactive material or a coated material on the gas reactive material determines the time at which the gas reactive material changes appearance after exposure to ambient air.

9. The containment system according to claim 1, wherein a size or shape of at least one of said plurality of atmospheric gas conduits can be modified to adjust a rate of the gas flow through the one of the plurality of atmospheric gas conduits.

10. A containment system for a plurality of products that are to be accessed in a timed sequence, the containment system comprising:
    a plurality of product compartments, each of said product compartments being adapted to hold at least one of said plurality of products;
    a plurality of gas sensitive indicators adapted to change appearance after exposure to ambient air, at least one of said gas sensitive indicators being located within a gas sensitive indicator window volume; and
    a plurality of atmospheric gas conduits each leading from one of the product compartments to one of said gas sensitive indicator window chambers, such that an exposure of one of said product compartments to gain access to a product in said one product compartment allows atmospheric gas to enter the product compartment and from there to flow through at least one of the plurality of atmospheric gas conduits that leads from said exposed product compartment to expose at least one of the gas sensitive indicators, the one gas sensitive indicator exposed to ambient air being arranged to change appearance in a manner that indicates that a next product in the timed sequence is to be accessed.

11. The containment system according to claim 1, further including a cover sheet providing instructions to a user pertaining to how to use the containment system.

12. The containment system according to claim 1, wherein the gas sensitive indicators are symbols, characters, images, or messages that become visible at the predetermined time after exposure to ambient air.

13. The containment system according to claim 1, wherein the product is a pill, capsule or tablet.

14. The containment system according to claim 1, wherein the product compartments are arranged in a linear array or matrix array pattern.

15. The containment system according to claim 14, wherein the gas sensitive indicator connected to a particular product compartment by one df the atmospheric gas conduits is positioned in proximity to a next product compartment in the linear array or matrix array pattern.

* * * * *